(12) United States Patent
Madsen et al.

(10) Patent No.: US 10,736,639 B2
(45) Date of Patent: Aug. 11, 2020

(54) APPLICATOR SYSTEM FOR APPLICATION OF SKIN TAG REMOVING DEVICES

(71) Applicant: TAGAWAY DEVICES APS, Rungsted Kyst (DK)

(72) Inventors: Niels Torp Madsen, Valby (DK); Poul Leo Anker, Birkerød (DK); Staffan Lennart Sundström, Helsingborg (SE)

(73) Assignee: TAGAWAY DEVICES APS, Rungsted Kyst (DK)

( * ) Notice: Subject to any disclaimer, the term of this patent is extended or adjusted under 35 U.S.C. 154(b) by 0 days.

(21) Appl. No.: 16/073,594

(22) PCT Filed: Feb. 1, 2017

(86) PCT No.: PCT/DK2017/050021
§ 371 (c)(1),
(2) Date: Jul. 27, 2018

(87) PCT Pub. No.: WO2017/133742
PCT Pub. Date: Aug. 10, 2017

(65) Prior Publication Data
US 2019/0038293 A1    Feb. 7, 2019

(30) Foreign Application Priority Data

Feb. 1, 2016  (DK) .................................. 2016 70050

(51) Int. Cl.
*A61B 17/122*     (2006.01)
*A61B 17/12*      (2006.01)
(Continued)

(52) U.S. Cl.
CPC ........ *A61B 17/1227* (2013.01); *A61B 17/128* (2013.01); *A61B 17/12009* (2013.01);
(Continued)

(58) Field of Classification Search
CPC ... A61B 17/083; A61B 17/0401; A61B 17/08; A61B 17/10; A61B 17/122;
(Continued)

(56) References Cited

U.S. PATENT DOCUMENTS

| | | |
|---|---|---|
| 2013/0123806 A1 | 5/2013 | Howlett et al. |
| 2014/0379004 A1 | 12/2014 | Raybin et al. |
| 2016/0183937 A1* | 6/2016 | Miraki ............... A61B 17/0467 606/143 |

FOREIGN PATENT DOCUMENTS

| | | |
|---|---|---|
| EP | 1 430 840 A2 | 6/2004 |
| GB | 2 322 802 A  | 9/1998 |

OTHER PUBLICATIONS

International Search Report and Written Opinion, Appl. No. PCT/DK2017/050021, dated May 16, 2017.
(Continued)

*Primary Examiner* — Wade Miles
*Assistant Examiner* — Mikail A Mannan
(74) *Attorney, Agent, or Firm* — Winston & Strawn LLP

(57) ABSTRACT

An applicator system that includes at least one skin tag removing device and an applicator for application of the device onto a skin tag. The device has an aperture delimited by occlusion members, and opposite flexible pressure members to apply pressure to the occlusion members towards the aperture. The applicator has a housing with a guideway extending between the inlet and outlet which receives at least part of an elongated reciprocating applicator rod having an applicator head for engaging the skin tag removing device when moved out of the outlet of the guideway and forced through the aperture of the skin tag removing device, and an opposite operating end located outside the inlet of the guideway. The applicator head has a space for accommo-
(Continued)

Figure 4:
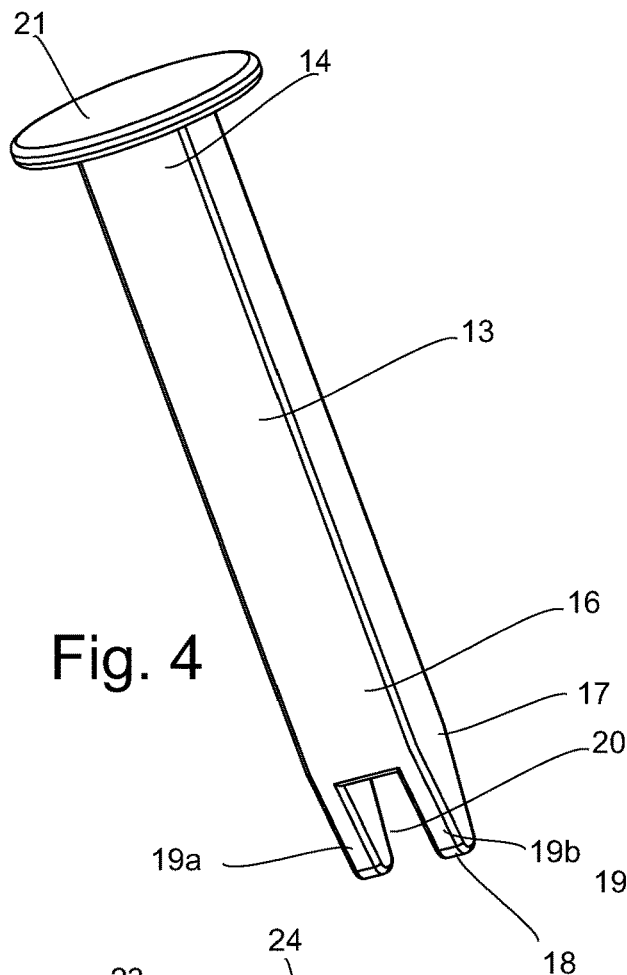

dating a skin tag and is configured for ejecting the device to occlude the skin tag which eventually withers away.

24 Claims, 20 Drawing Sheets

(51) Int. Cl.
*A61B 17/128* (2006.01)
*A61B 17/50* (2006.01)
*A61B 50/30* (2016.01)
*A61B 17/54* (2006.01)
*A61B 17/08* (2006.01)
*A61B 17/10* (2006.01)
*A61B 17/00* (2006.01)
*A61B 50/00* (2016.01)

(52) U.S. Cl.
CPC .............. *A61B 17/50* (2013.01); *A61B 17/54* (2013.01); *A61B 50/30* (2016.02); *A61B 17/083* (2013.01); *A61B 17/10* (2013.01); *A61B 2017/00761* (2013.01); *A61B 2050/006* (2016.02); *A61B 2050/3008* (2016.02)

(58) Field of Classification Search
CPC .......... A61B 17/1227; A61B 17/12009; A61B 2017/00747; A61B 17/00761; A61B 17/0427; A61B 17/0445; A61B 17/0464; A61B 17/12004; A61B 50/30; A61B 17/128; A61B 17/50; A61B 17/54; A61B 2017/00761; A61B 2017/00774; A61B 17/308
See application file for complete search history.

(56) References Cited

OTHER PUBLICATIONS

International Preliminary Report on Patentability (Chapter II), Appl. No. PCT/DK2017/050021, dated May 11, 2018.

* cited by examiner

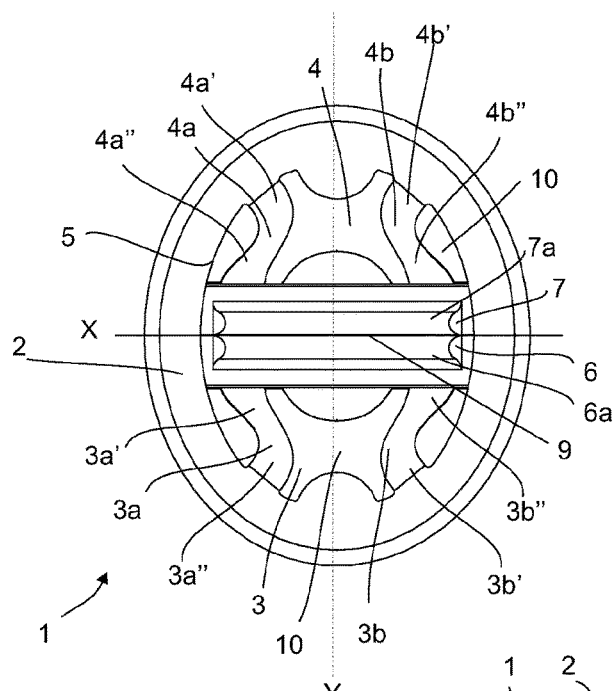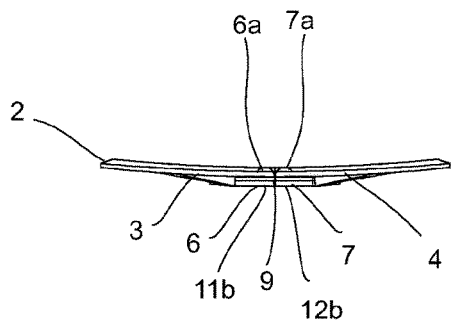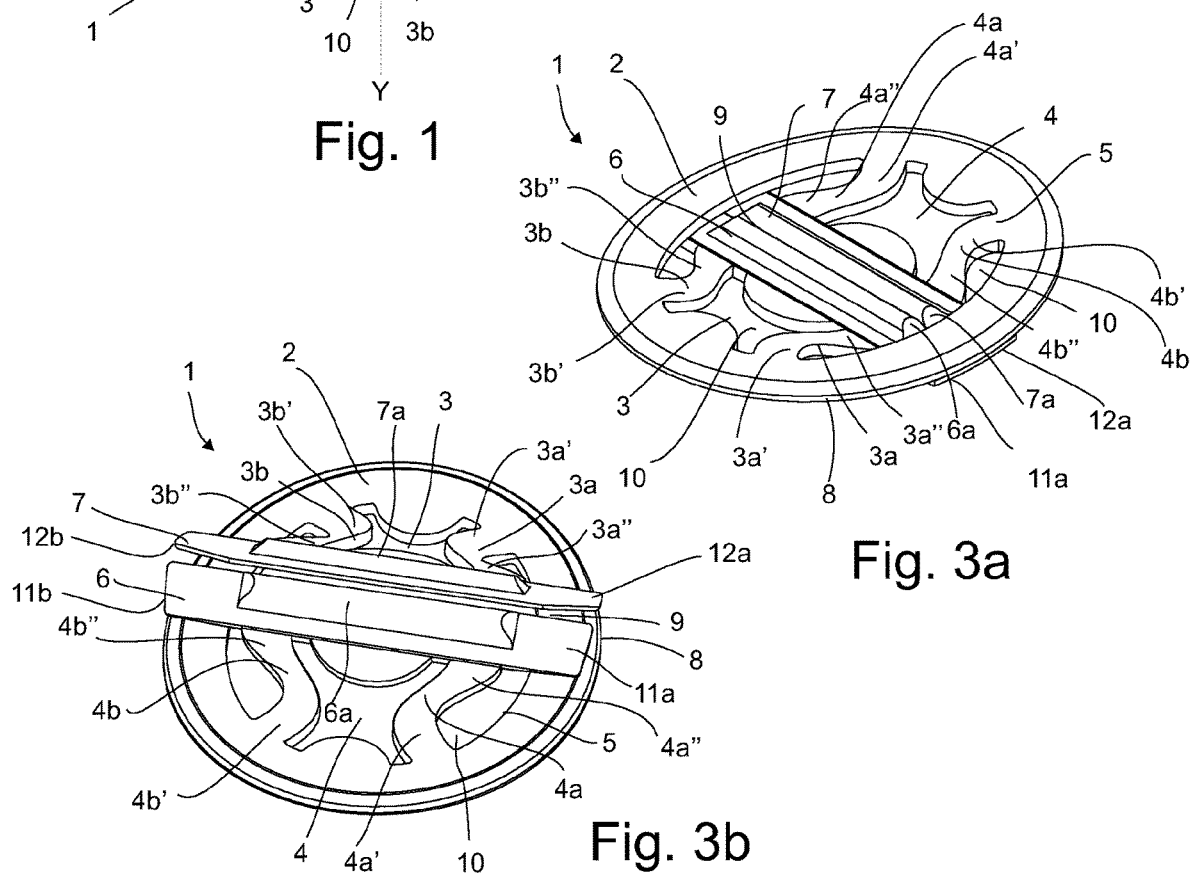

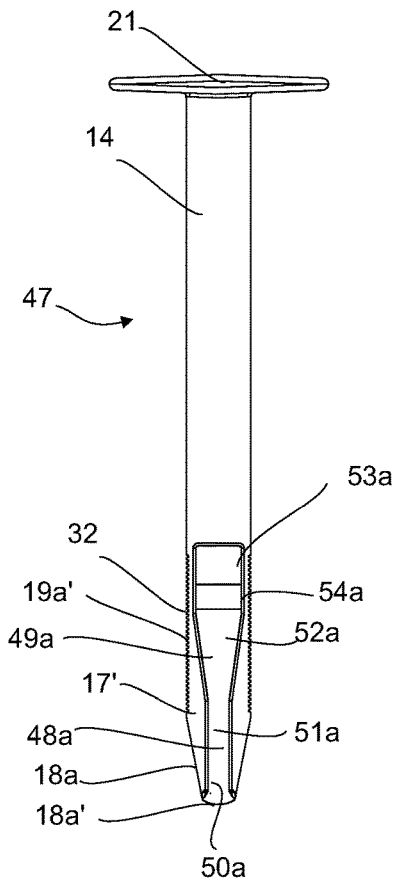
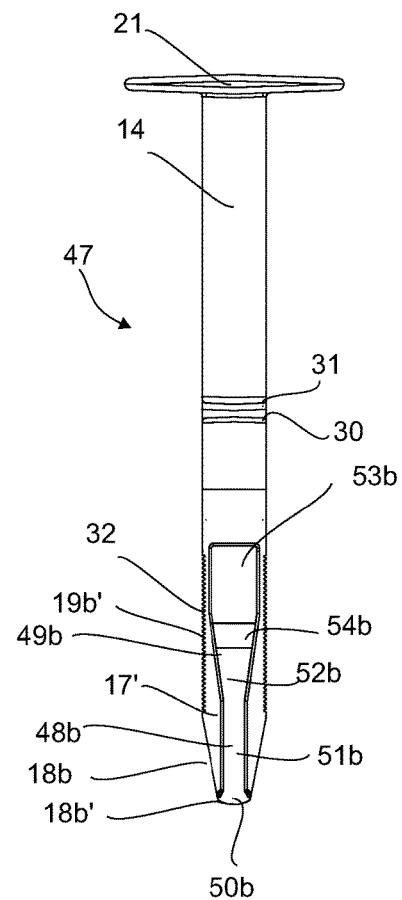
Fig. 23
Fig. 24
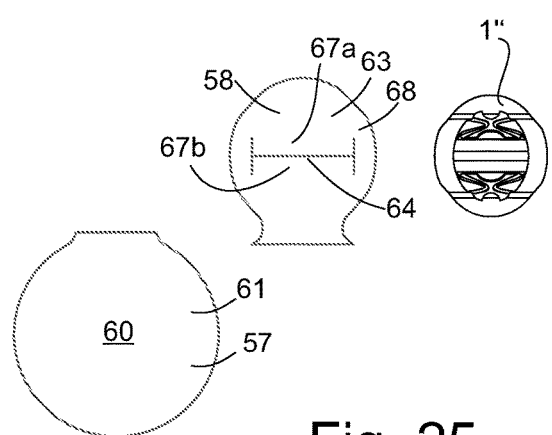
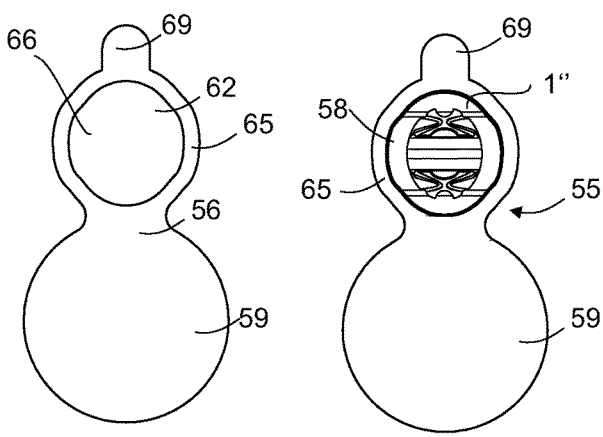
Fig. 25
Fig. 26

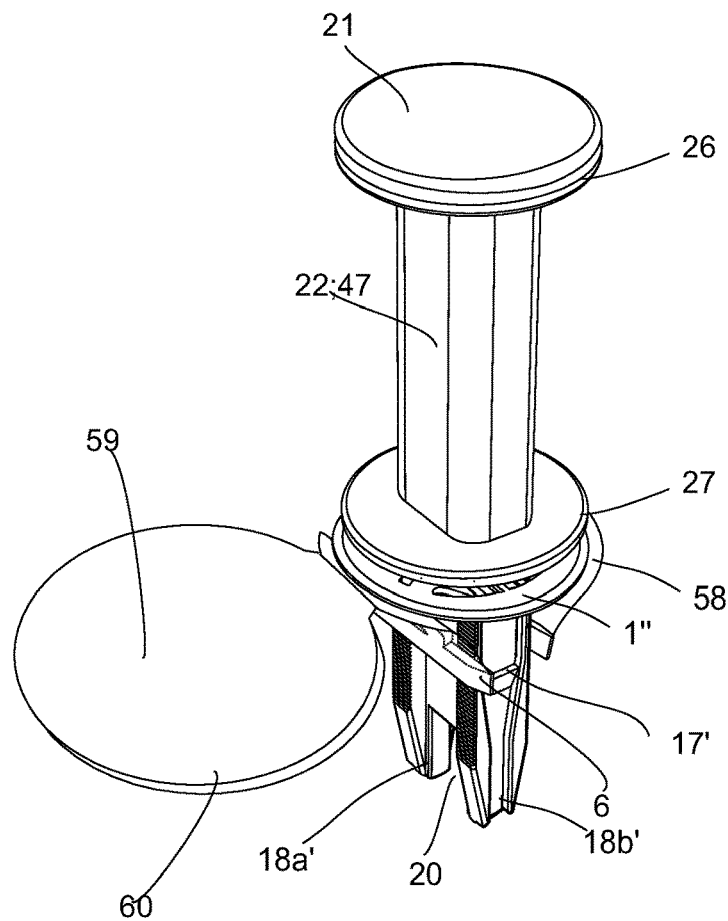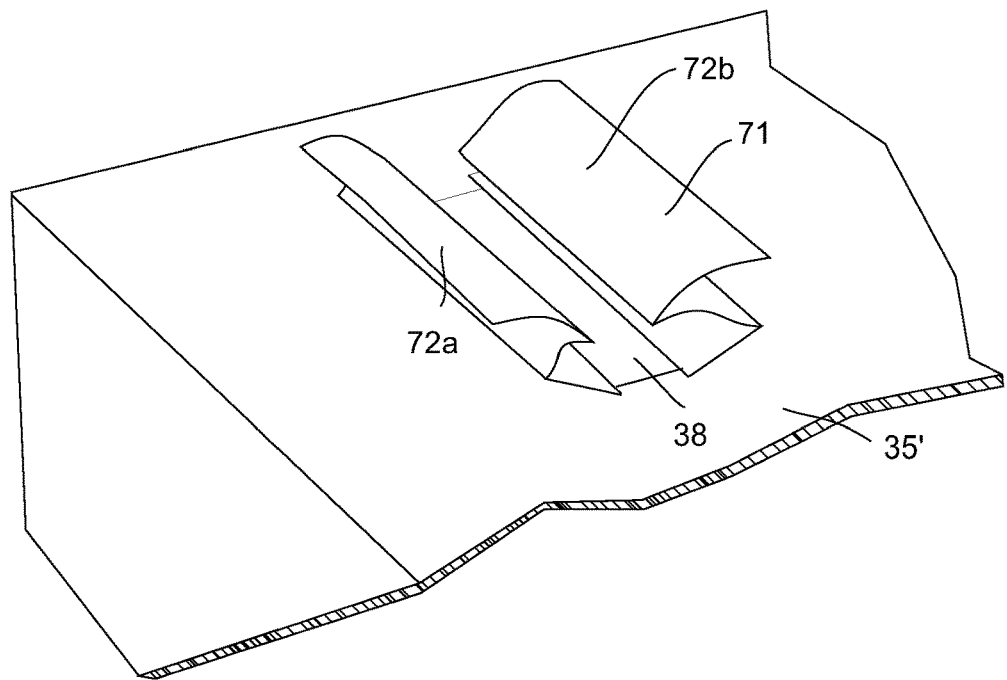
Fig. 38

APPLICATOR SYSTEM FOR APPLICATION OF SKIN TAG REMOVING DEVICES

This application is a 371 filing of International Patent Application PCT/DK2017/050021 filed Feb. 1, 2017, which claims the benefit of Danish application no. PA 2016 70050 filed Feb. 1, 2016.

BACKGROUND

The present invention relates to an applicator system comprising at least one skin tag removing device and an applicator for application of the skin tag removing device on a skin tag, wherein the skin tag removing device is of the kind that has an aperture delimited by occlusion members, and opposite flexible pressure members to apply pressure to the occlusion members towards the aperture. The applicator comprises a housing with a guideway that extends between an inlet and an outlet, which guideway is provided for receiving at least a part of a reciprocating applicator rod, which applicator rod has a length that is longer than the length of the guideway, an applicator end provided with an applicator head for engaging the skin tag removing device when the applicator head is moved out of the outlet of the guideway and forced through the aperture of said skin tag removing device, and an opposite operating end located outside the inlet of the guideway, and the applicator head has a space for accommodating a skin tag.

Skin tags, acrochordons, are not skin cancers and cannot turn into skin cancers. A skin tag is simply a soft, often very disfiguring and annoying growth that hangs from the skin surface on a thin pedicle. The skin tag varies in size and shape, but the larger they are the more annoying and disfiguring. Moreover their physical presence may cause other problems, e.g. when shaving and washing, and there is a huge desire to have skin tags eliminated for cosmetic reasons.

Surgical intervention is normally required for removal of skin tags. Pedunculated skin tags are removed by trained medical staff, e.g. by excising with scissors, forceps, electro-desiccation, or cryotherapy. The oldest known way of removing a skin tag is however simple ligation with a suture. Gradually the pressure from the suture on the skin tag reduces as the diameter of the pedicle gets smaller, so the ligating effect of the suture becomes poorer and poorer, resulting in inadequate ligation and prolonged and inefficient removal of the skin tag. The need for making a second and tighter ligature around the pedicle of the skin tag to optimize constriction and eventually completely obstruct blood flow through the pedicle may even arise.

So the above methods either require surgical intervention or a long-lasting and unreliable ligating with a series of sutures.

As alternatives to the above methods the applicant has recently proposed new skin tag removing devices that can be used to occlude, or occlusively remove, one or more of the variety of skin tags. Such devices are e.g. disclosed in the applicant's International patent applications no. PCT/IB2011/000265 and PCT/IB2005/054334.

The skin tag removing device known from PCT/IB2011/000265 constricts the pedicle of the skin tag to occlude and terminate blood flow to the skin tag. A base member of the skin tag removing device has an aperture that surrounds the skin tag. Opposite pressure members apply pressure to opposite occlusion members to constrict the pedicle of the skin tag by applying an occlusion force sufficient to occlude blood flow to said skin tag. Subjected to such treatment the skin tag eventually falls off. The intention is to arrange this known skin tag removing device simply by bending it by using the fingers to open the aperture sufficiently to pass over an enlarged head of the skin tag and arrange the occlusion members around the pedicle as clamping jaws. However, this skin tag removing device must at the same time be made so small that it is comfortable to wear during the treatment period, and as result of this smallness only a very limited area is available for grasping and manipulating by the fingers to open the aperture and arrange the skin tag removing device on the skin tag.

So some people experience difficulties when the aperture of the skin tag removing device is to be guided over the skin tag for the pressure members and the occlusion members to be arranged in functional operative state to stop blood flow to the skin tag.

The applicant's above-mentioned known skin tag removing devices have been shown to be extremely effective for treatment of skin tags, however the manner they are placed on a disfiguring skin tag can still be optimized and standardized.

Accordingly, it is a main aspect of the present invention to facilitate application of a skin tag removing device on a skin tag, such as facilitating application of the skin tag removing devices known from the applicants International patent applications no. PCT/IB2011/000265 and PCT/IB2005/054334.

It is yet an aspect of the present invention to provide an applicator system of the kind mentioned in the opening paragraph by means of which a skin tag removing device can be mounted on a skin tag faster and easier than hitherto known.

It is yet an aspect of the present invention to provide an applicator system of the kind mentioned in the opening paragraph by means of which an aperture of a skin tag removing device can be brought to surround the pedicle of a skin tag without touching said skin tag removing device with the fingers.

It is yet an aspect of the present invention to provide an applicator system of the kind mentioned in the opening paragraph by means of which skin tag removing devices can be mounted on a skin tag in a substantially standardized manner.

It is yet an aspect of the present invention to provide an applicator tool for facilitating application of skin tag removing devices of the kind having an aperture between opposite pressure members and opposite occlusion members.

It is yet an aspect of the present invention to provide an efficient skin tag removing device suited for use with the applicator system.

The novel and unique whereby these and other aspects are achieved according to the present invention consist in that the applicator head of the applicator end is bifurcated, whereby said head is divided into two opposite branches, parts or legs, and the space is delimited between said at least two opposite branches, parts or legs.

The different lengths allow the applicator head of the applicator end to reciprocate inside and outside the guideway. The operating end is used to operate the applicator end to expose the applicator head outside the outlet of the guideway to engage the skin tag removing device, and can also be used to retract the applicator head inside the guideway. In operation the applicator head of the applicator end of the applicator rod is fitted with a skin tag removing device by forcing the applicator head into and through the aperture to open said aperture sufficiently to pass over a skin tag. At the same time the occlusion members are spread apart, and consequently the inserted applicator head applies a tensioning force to the occlusion members and the pressure members. In the next step the applicator head is brought in contact with the skin surface so that the space of the applicator head of the applicator is arranged to accommodate the skin tag. Finally the housing is moved towards the skin surface forcing the skin tag removing device in front of it. The applicator head of the applicator end is thereby retracted inside the guideway, and the skin tag removing device looses the engagement with the applicator head, whereby the tensioning force is relieved and the pivoted pressure members can return the occlusion members to close the aperture around the pedicle of the skin tag.

The applicator head of the applicator end is bifurcated.

Within the context of the present invention the term "bifurcated" in relation to the applicator head means that said head is divided into two opposite branches, parts or legs. The space is delimited between said at least two opposite branches, parts or legs. The bifurcation may however include additional branches, parts or legs that all together delimit the space in form of a cavity, gap, compartment suited for inserting a skin tag that is to be treated with a skin tag removing device of the kind adapted for the applicator system according to the present invention.

In the simplest bifurcated embodiment the space is delimited by two opposite legs, e.g. of a length corresponding to at least the height of a small skin tag, such as between 0.3 mm-0.6 mm. When the applicator head of the applicator end is inserted in the aperture of the skin tag removing device the pressure members pivot and the occlusion members of the skin tag removing device clamp against the applicator head, preferably above the delta of the bifurcation so that the gap, the space, between the two opposite branches, parts or legs is entirely available for accommodating the entire skin tag. These branches, parts or legs may have axes substantially parallel to the axis of the reciprocating applicator rod. The branches, parts or legs can easily be arranged exterior to the skin tag along the pedicle, with the skin tag located in the space between the legs. The skin tag removing device is in this position preferably located above or around the head of the skin tag itself, but is rapidly moved towards the skin upon a downwards travel of the housing. So the housing drives the skin tag removing device rapidly off the applicator head to immediately snap onto the skin tag with optimum occlusion force applied to the occlusion members by the returning of the pressure members attempting to close the aperture again.

When the applicator rod is retracted or when the housing travels downwards away from the operating end, the applicator head is withdrawn inside the guideway. The temporarily engaged skin tag removing device comes along until it is set free of the applicator head of the applicator end upon hitting the outlet. The tensioning force previously applied by the applicator end to the pressure members are released, and the opposite occlusion members come together and squeeze around the pedicle as jaws, to effectively ligate the pedicle until blood supply eventually stops and necrosis of the skin tag sets in. The diameter of the pedicle gradually decreases during the occlusion process, however the flexible pressure members keep on applying pressure to the occlusion members to thereby at all times maintain sufficient occlusion to occlude blood supply to the skin tag. Eventually the elimination of blood supply to the skin tag causes the skin tag to wither away, thus severing the skin tag from the skin. The skin tag falls off without any bleeding and without surgical intervention.

The interior space of the applicator head is large enough to accommodate a skin tag, and the exterior dimensions, shape and configuration of the applicator head is sized to pass into the aperture to deflect the occlusion members and enlarge the aperture to arrange the space around the skin tag. So the part of the applicator head of the applicator end that has the space must be so long that it can both reach over the skin tag and carry the skin tag removing device without it accidentally gets loose.

One preferred skin tag removing device for the applicator system of the present may comprise a ring-shaped base member having a central opening and two opposite flexible pressure members pivotally attached to the ring-shaped base member, and oppositely said attachment to the ring-shaped member having a respective associated occlusion member. The occlusion members protrude towards each other and define in-between them the aperture for inserting the applicator head for preparing the skin tag removing device for mounting on the skin tag and for surrounding and clamping around said skin tag. To that purpose the occlusion members can be configured as clamping jaws, such as elongated flat rods or thin webs, suited to occlude the pedicle of the skin tag as a result of the pressure members attempting to return to the most relaxed condition after having been kept pivoted by the inserted applicator head. The occlusion members may be longer than the width or diameter of the central opening, so that their opposite free ends can engage the underside of the ring-shaped base member for obtaining a pre-tensioning and/or alignment of the pressure members. The slight deviation of the occlusion members from the plane of the ring-shaped base member indicates the direction for further pivoting of the occlusion members away from the underside and plane of said ring-shaped base member.

This configuration of pivotable pressure members of the skin tag removing device acts as opposite spring mechanisms with in-built shape-memory. When the pressure members are pivoted apart by the introduction of the applicator head of the applicator end, these spring-mechanisms becomes tensioned, and constitute the means responsible for returning the occlusion members towards the underside of the base member.

The occlusion members can advantageously have lengthwise reinforcing members to improve dimensional strength when the applicator head passes through. Some applicator heads of the present invention can have protruding features, such as beads, shoulders or keys, to control and guide movement of the applicator head inside the aperture of the skin tag removing device, in which case it is beneficial if the reinforcing members are shorter than the occlusions members to give space for features protruding from the base member of the skin tag removing device inside the central opening of said skin tag removing device.

The skin tag removing device can advantageously be included in a skin tag removing unit including an adhesive layer, an adhesive cover, and a release liner for protecting the adhesive. This way the adhesive cover is presented associated with the skin tag removing device ready-for-use by being arranged in a defined position for subsequent coverage of the occluded skin tag. The adhesive layer provides an easy way to apply adhesive to the skin-contacting face of the skin tag removing device.

In a preferred design said release liner has a figure-eight-shape with a first part having a first diameter that is larger than a diameter of a second part. The second part is the release liner part for the adhesive layer, thus the layer for making a non-adhesive skin tag removing device adhesive, and the first part is the release liner part for the adhesive cover, which adhesive cover advantageously simply can be a plaster component.

To avoid direct contact between skin and the annular exterior edge of the skin tag removing device in use, which might injure or harm the skin, it may be beneficial if the adhesive layer is larger than the skin tag removing device, such as to expose a annular rim of the adhesive layer beyond the skin tag removing device. To protect the adhesive at said annular rim the second part of said release liner may be divided into a ring-shaped release part around a central release part, which central release part conveniently may be of a size and outline corresponding to that for the skin tag removing device. The ability to separate the ring-shaped release part from the central release part that allows individual detachment can e.g. be conferred to the release liner by kiss cutting.

To be able to pass into the aperture of the skin tag removing device to enlarge it further the largest exterior distance between opposite legs of the bifurcated applicator head is smaller than the width of the opening of a ring-shaped base member of the skin tag removing device, which width also defines the length of the aperture for inserting the applicator head. The occlusion members are below the underside of the ring-shaped base member.

The inlet of the guideway of the housing may have a first stopper for engaging at least one second stopper of the applicator rod. Such engagement serves for preventing the rod from being withdrawn from the guideway when the applicator head of the applicator end is moved from outside the outlet of the guideway inside said guideway, e.g. when the skin tag removing device is set free of the applicator head of the applicator end. An exemplary first stopper can be one or more small protrusions or beads facing inside the inlet or inside the guideway, or a slightly reduced area or diameter of the inlet compared to the area or diameter of the outlet. The second stopper can e.g. be one or more axially extending leaf springs acting along the axis of the applicator rod above the applicator head so that the leaf spring e.g. hits on the protrusion at or in the vicinity of the inlet.

Further or alternative means to improve and/or restrict travel of the applicator rod in the guideway are within the scope of the present invention. The wall of the guideway and the applicator rod can have co-operating ratchet means, in which case the travel becomes tactile and subject to a frictional force. If very smooth travel is preferred one or both of the guideway and the applicator rod can have a liner of coating to reduce friction.

In a modified embodiment of a skin tag removing device of the present invention, said skin tag removing device can have opposite guide beads or guide keys that protrude towards each other inside the central opening of the skin tag removing device from the interior diameter of the ring-shaped base member. The opposite guide beads or guide keys can then be configured to engage co-operative guide grooves provided on exterior opposite faces of the applicator head so that the skin tag removing device cannot be displaced or rotate around the applicator head when operated.

The guide grooves of the applicator head may have a respective key opening located at a free tip part of the applicator head, e.g. a tapered free tip part of the applicator head, to allow easy entry of a guide bead or a guide key of the skin tag removing device when the applicator head contacts said skin tag removing device, and to allow the applicator head to set the skin tag removing device free again on a skin tag when the applicator head is retracted from the housing, thus when the housing is moved towards the free end of the applicator head driving the skin tag removing device in front of the housing.

In one design of the guide grooves of the applicator head the key opening can extend into a respective distal elongate guide groove section, which distal elongate guide groove section can extend further into an intermediate guide groove section that has a width that increases towards a blind proximal elongate guide groove section. A shoulder located protruding from a guide groove of the applicator head serves to limit and gently obstruct the level of travel of the guide beads or guide keys of the skin tag removing device along the associated guide groove once the skin tag removing device is mounted to the applicator head. The shoulder may be located at the same or different axial distance from the key opening, so that the skin tag removing device is allowed to move axially on the applicator head to same or different degree, in particular in the situation wherein the skin tag removing devices is to be released from a holder component as described below.

The housing may have a circumferential outlet flange surrounding the outlet. The circumferential outlet flange serve to assist in disengaging a skin tag removing device mounted on the applicator head of the applicator end. When the housing performs a downwards travel towards and along the applicator head, the outlet flange conveniently moves the skin tag removing device in front of it until the skin tag removing device is set free of the applicator head and engages a skin tag arranged in the space of the applicator head.

The operating end of the applicator rod may have a finger press button, preferably having an area larger than the inlet of the housing to avoid that the finger press button moves inside the guideway and jams the travel, e.g. by getting below the first stopper. The presence of the finger press button provides inherent guidance to use the applicator rod and improves operation of the applicator system. An inlet flange arranged surrounding the inlet of the guideway may be a further means to stop the downwards travel of the applicator rod towards the outlet of the guideway. The inlet flange and the outlet flange provide the housing with a reel appearance that is very easy to grasp when the housing is moved to disengage the skin tag removing device from the applicator head.

In a preferred embodiment the exterior surface of at least the applicator head of the applicator end has means to temporarily maintain the engaging position of the skin tag removing device on the applicator end until the skin tag removing device is to be applied on the skin tag. Such means can be obtained by making at least a part of the surface of the applicator end, in particular the applicator head, uneven or providing it with a friction liner or coating. An uneven surface can e.g. be ridged or serrated.

The applicator system further comprises a holder component, which holder component serves for facilitating arranging at least one skin tag removing device on the applicator head of the applicator end without the need to hold the skin tag removing device between the fingers. The holder component is structured to elevate a mounting plane of the holder component above a support plane for the holder component, so that the applicator head of the applicator end can pass freely towards the aperture of the skin tag removing device to safely and efficiently engage said device. The distance between the mounting plane and the support plane can thus conveniently correspond to the length of the applicator head or be longer.

The holder component has a top wall defining the mounting plane, as well as a mounting surface for the skin tag removing device, and at least one hole through the top wall, which at least one hole has a hole diameter that is smaller than the smallest exterior width or smallest exterior diameter of the skin tag removing device but larger than the length of the occlusion members, to allow the occlusion member to pass through the hole in the top wall and still prevent the entire skin tag removing device from being forced through the hole.

So a hole in the top wall may be dimensioned to allow the at least one skin tag removing device to rest on at least a part of the top wall of the holder component along the perimeter of the hole so that the aperture is free to allow the applicator head of the applicator end to pass through the aperture of the at least one skin tag removing device to engage the at least one skin tag removing device. Engagement takes places in the condition of the applicator wherein the applicator head of the applicator end is displaced out through the outlet of the guideway of the housing so that said applicator head can act to pivot the pressure members with associated occlusion members below the top wall when the applicator head is forced into the aperture. The tip of the applicator head may hit the support plane, but need not do so if the distance between the support plane and the top wall is longer than the length of the applicator head.

Said distance can be obtained by a circumferential wall along the top wall in which case the holder component is substantially box-shaped, which box-shape can be open or closed by a bottom wall. Alternatively, several spacers or legs can protrude from the top wall so that the holder component can rest on the support plane like a table on a floor. The height of the circumferential wall or the length of the spacers or legs defines the elevated distance and provides a mounting chamber or mounting space below the top wall of the holder component.

The top wall of the holder component may have an adhesive, e.g. an adhesive layer or coating, around the holes to realisably keep the skin tag removing device(s) stuck to the top wall, such as during storage and during introduction of the applicator head. Alternatively, the adhesive can be provided on the underside of the skin tag removing device to be utilised for adhering the skin tag removing device to the skin. A detachable cover may be provided to protect the skin tag removing device on top of the top wall prior to use. The cover can in some embodiments expediently be reused for coverage of the occluded skin tag during the occlusion period in the operative state of the skin tag removing device. Suitable release liners may be included to facilitate attachment and detachment of skin tag removing device and cover at and from the top wall.

The adhesive force between skin tag removing device and the holder component needs to be overcomed without the skin tag removing device gets off the applicator head when the applicator is retracted from the holder component. A careful choice of kind, amount and pattern of adhesive can minimize this potential problem. However, in other embodiments the holder component can advantageously have one or more flexible release structures around one or more of the holes. A respective skin tag removing device or skin tag removing unit can then be mounted or be mountable to said flexible release structure which flexible release structure then contributes to a smooth detachment of the skin tag removing device from the holder component. The flexible release structure comes along when the skin tag removing device is lifted away from the holder component using the applicator whereby the adhesive layer or adhesive skin-contacting face of the skin tag removing device gradually can be pulled off the flexible release structure at the same time.

The flexible release structure can for example include at least two opposite release structure parts arranged on opposite sides of the hole to attach to opposite sections of e.g. a double-coated adhesive layer of the skin tag removing device.

A suitable release structure part can e.g. be a pleated piece of release liner, e.g. a release liner in form of a silicon paper. When the applicator head of the applicator is inserted between the occlusion members said applicator head will inherently push the flexible release structure down inside the associated hole of the holder component, just a little, and this way initiate a first initial detachment between the skin tag removing device and the flexible release structure, and so that the subsequent moving of the applicator head up again from the hole will continue the detachment process which has already started locally. Adhesive detachment may thus start in one or more small areas or one or more points and then spread in response to moving the applicator upwards and away form the holder component until complete detachment has been achieved in a smooth and gentle manner.

The pleated release liner structure is just one embodiment of a flexible release structure and alternatives are within the scope of the present invention. Alternative release structures may include, but are not limited to bellows, spongy materials, elastic materials, spirals, etc. So any design and/or material that is able to expand and contract to trigger an onset of detachment and subsequent gradually detachment of the adhesive layer or the adhesive tag removing device is within the scope of the present invention.

The invention further relates to a method of operating the applicator system described above.

The method comprises obtaining temporarily engagement between the applicator head and the skin tag removing device by displacing the applicator head of the applicator end of the applicator through the aperture of the skin tag removing device thereby spreading the occlusion members apart by pivoting the pressure members. The tensioning of the pressure members provides the pressure force utilized to firmly engage the skin tag removing device onto the applicator head of the applicator end.

To eject the skin tag removing device the applicator head of the applicator end is simply moved inside the guideway thereby releasing the pressure force and restricting the aperture. This step can be done either by moving the housing towards the operating end of the applicator rod, or by pulling the applicator rod to withdraw it's applicator head inside the guideway.

The method can advantageously further comprise some preparation steps prior to the engagement between the applicator head and the skin tag removing device, wherein such preparation step can include preparation step a) of providing the skin tag removing device as part of a skin tag removing unit, e.g. the skin tag removing unit discussed above, and wherein an adhesive or an adhesive layer is selected and provided to confer an adhesive property to the skin tag removing device. A release liner may serve to protect one or both of the adhesive of the adhesive cover and the adhesive or adhesive layer adapted for conferring a skin-adhesive property to the skin any adhesive surface prior to intended use, and to protect the adhesive from drying out.

The method can further comprise preparation step b) of providing a holder component including a flexible release liner structure, e.g. the holder component discussed above, in association with a hole at a top wall of said holder component, and preparation step c) of adhering the skin tag removing unit to said flexible release liner structure, to obtain the possibility of initiating a release locally at a limited area or one or more points of adhesive contact between the flexible release structure and the adhesive skin-contacting surface or adhesive layer.

The method may comprise a release step after the temporarily engagement between the applicator head and the skin tag removing device, said release step includes moving the applicator with engaged skin tag removing device upwards from the holder component until the adhesive skin-contacting face of the skin tag removing device is released from its adhesive attachment to the flexible release structure. The adhesive contact is initially large and the adhesive contact force thus corresponding large over the entire adhesive contact area between flexible release structure and skin tag removing device. In the absence of a flexible release structure there is a risk that the adhesive skin tag removing device may not separate easily from the holder component, with the potential consequence that the skin tag removing device is unable to stay mounted on the applicator head when the applicator is pulled upwards from the holder component.

Accordingly in a preferred embodiment the release step may include local and/or gradual release of the adhesive skin-contacting face of the skin tag removing device from its adhesive attachment to the flexible release structure until complete release from the holder component and flexible release structure has taken place. The flexible release structure is thus of the kind adapted for such a release step.

The invention will be described in further details below wherein

Figure 5:
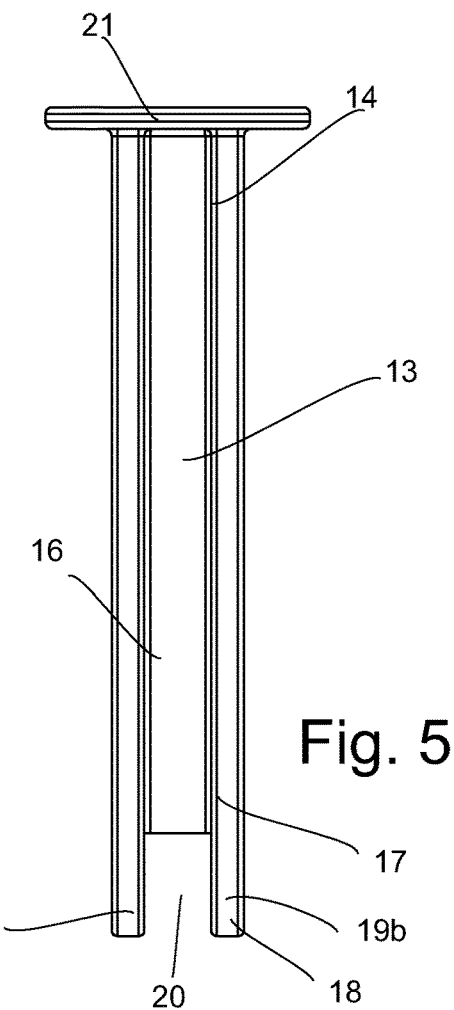
Figure 6:
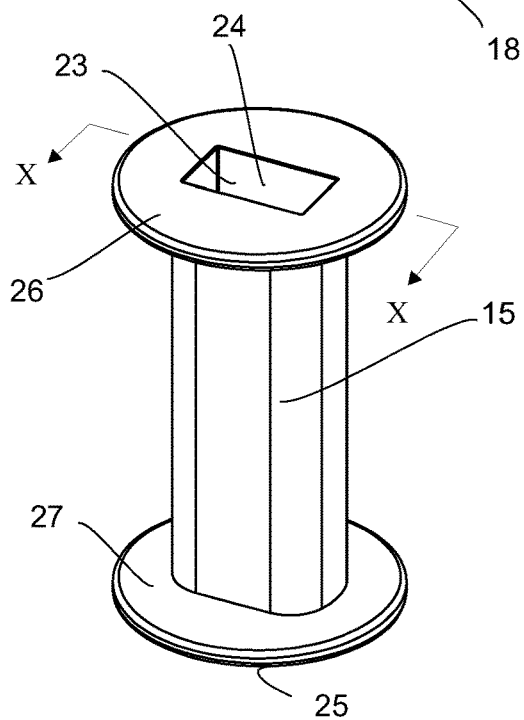
Figure 7:
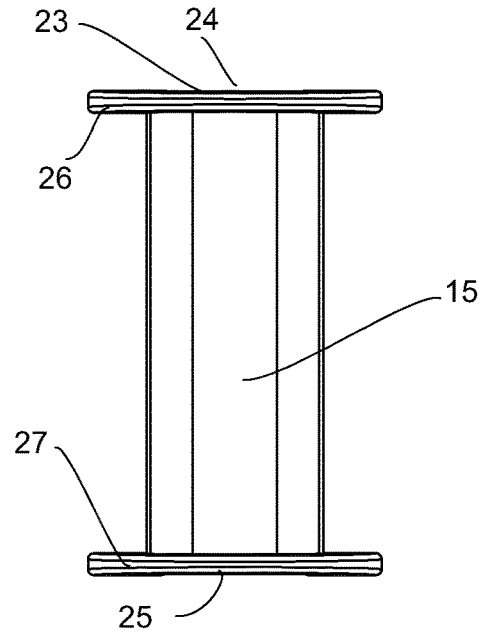
Figure 8:
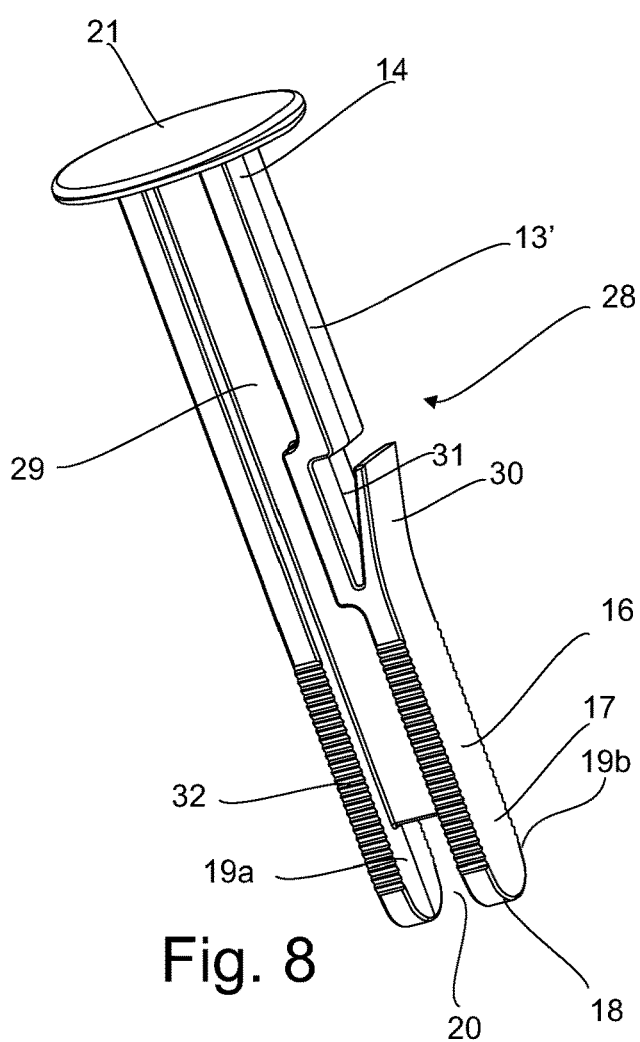
Figure 9:
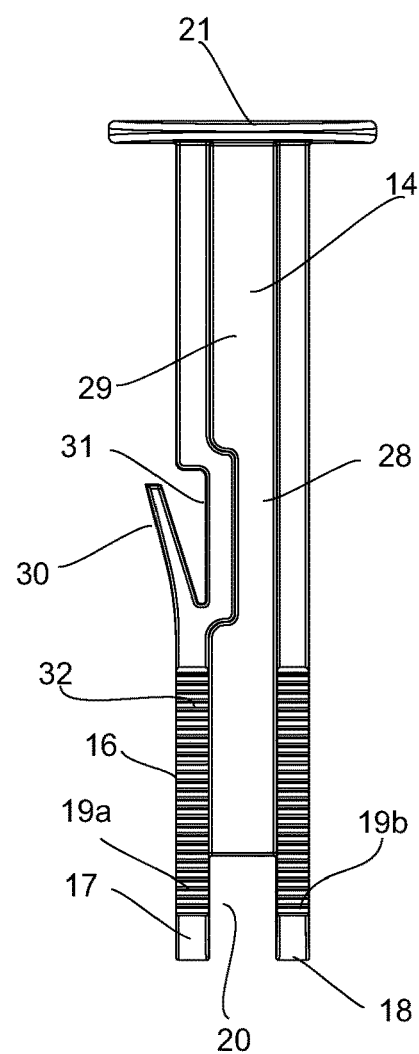
Figure 10:
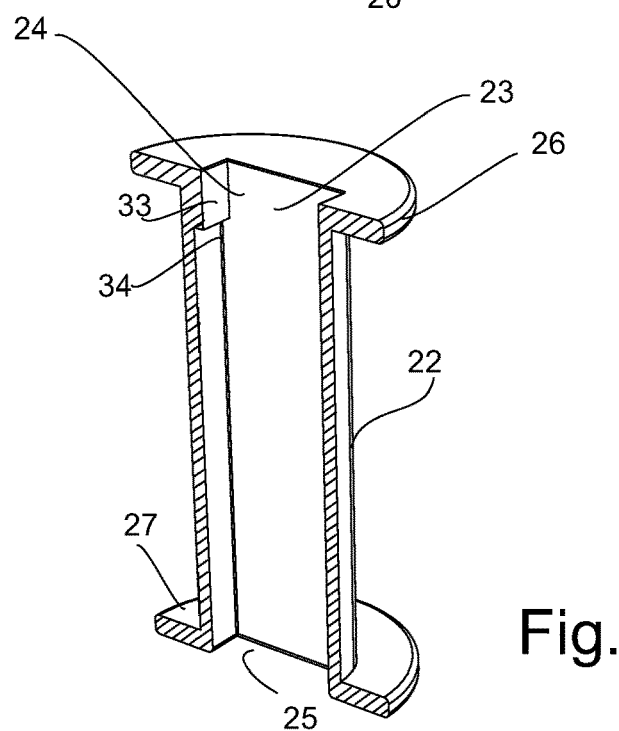
Figure 11:
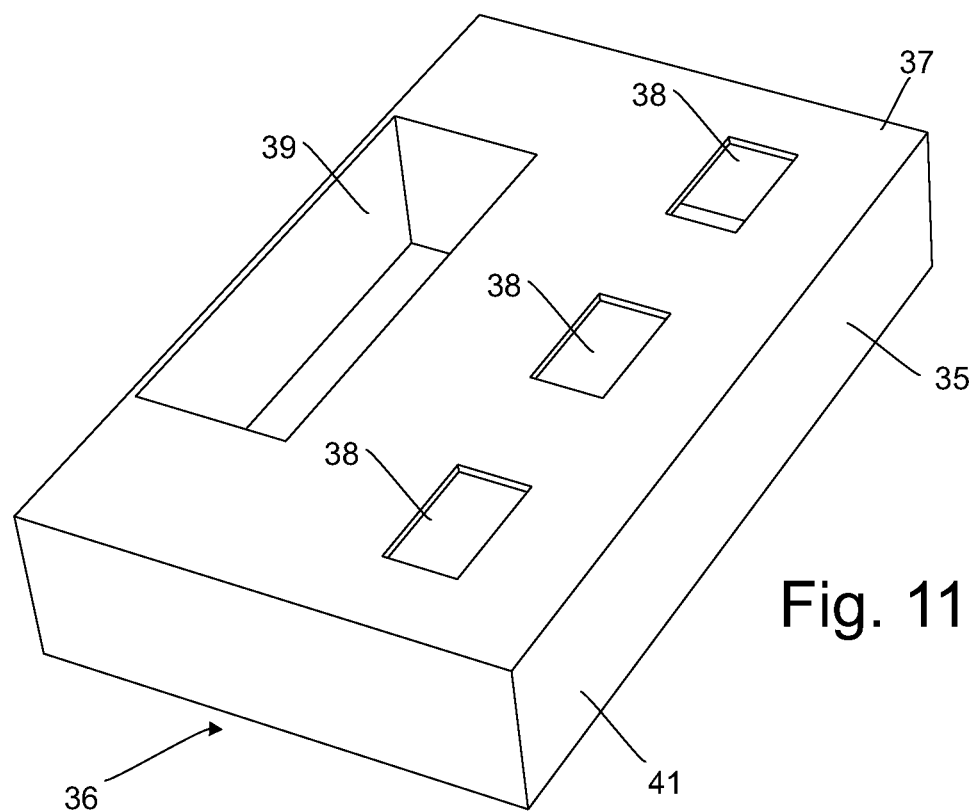
Figure 12:
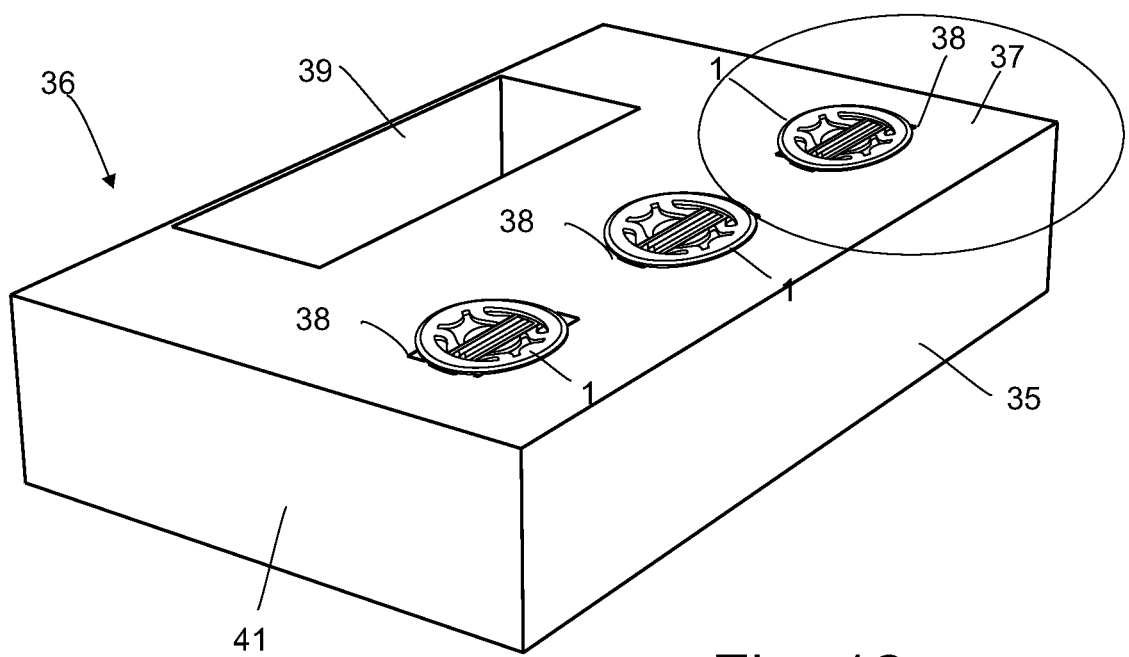
Figure 13:
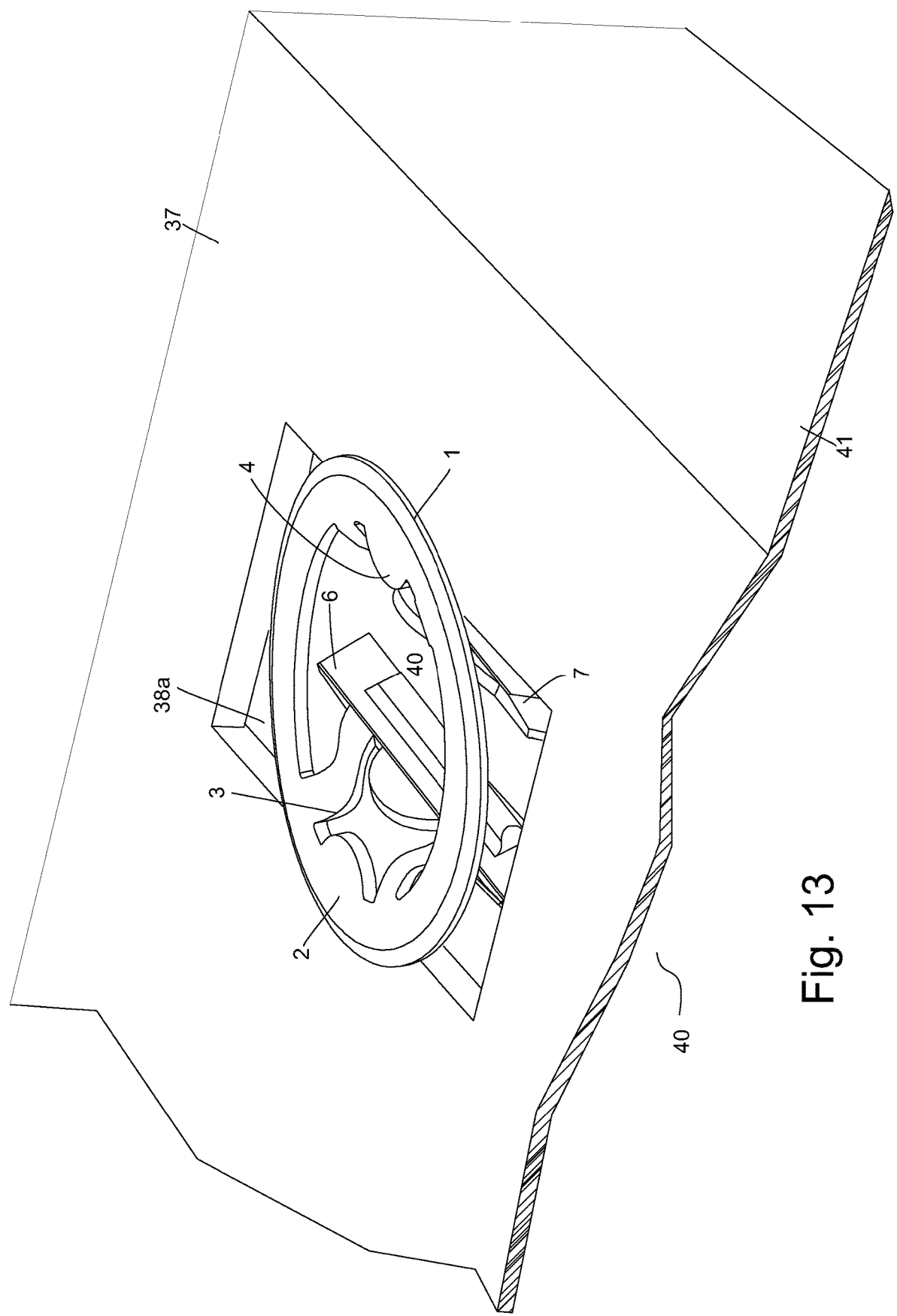
Figure 14:
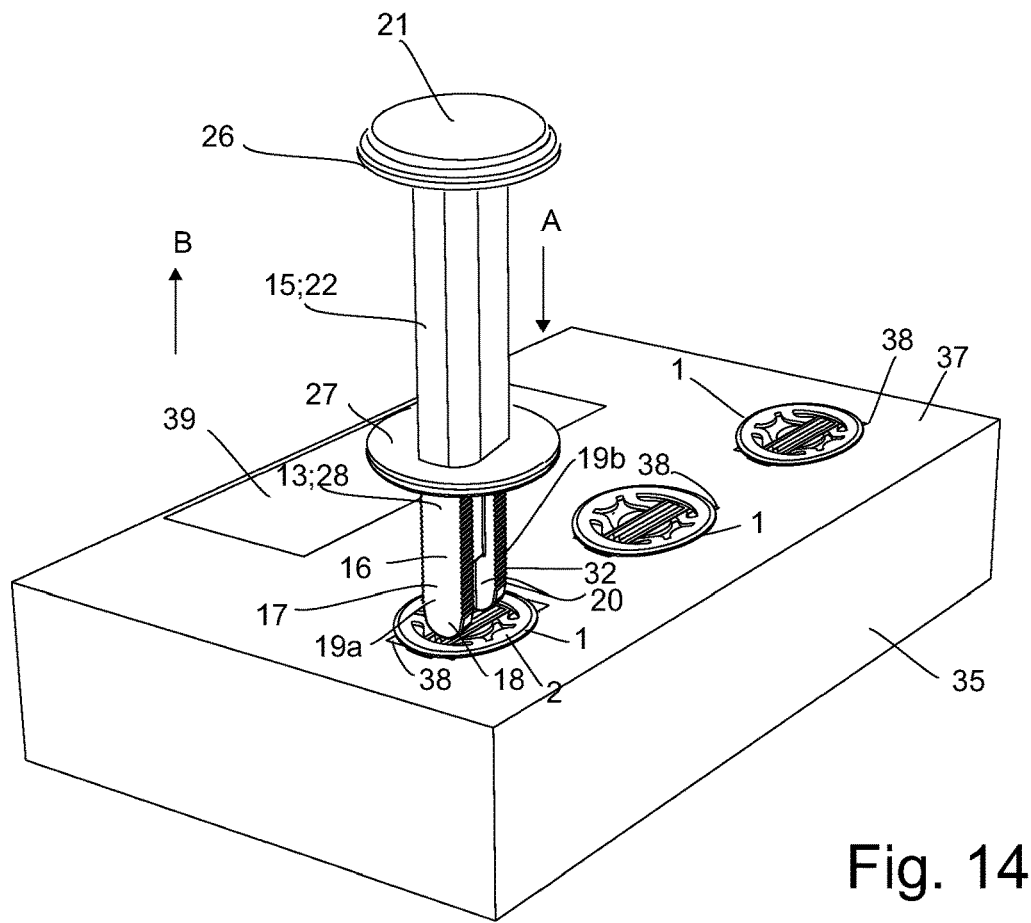
Figure 15:
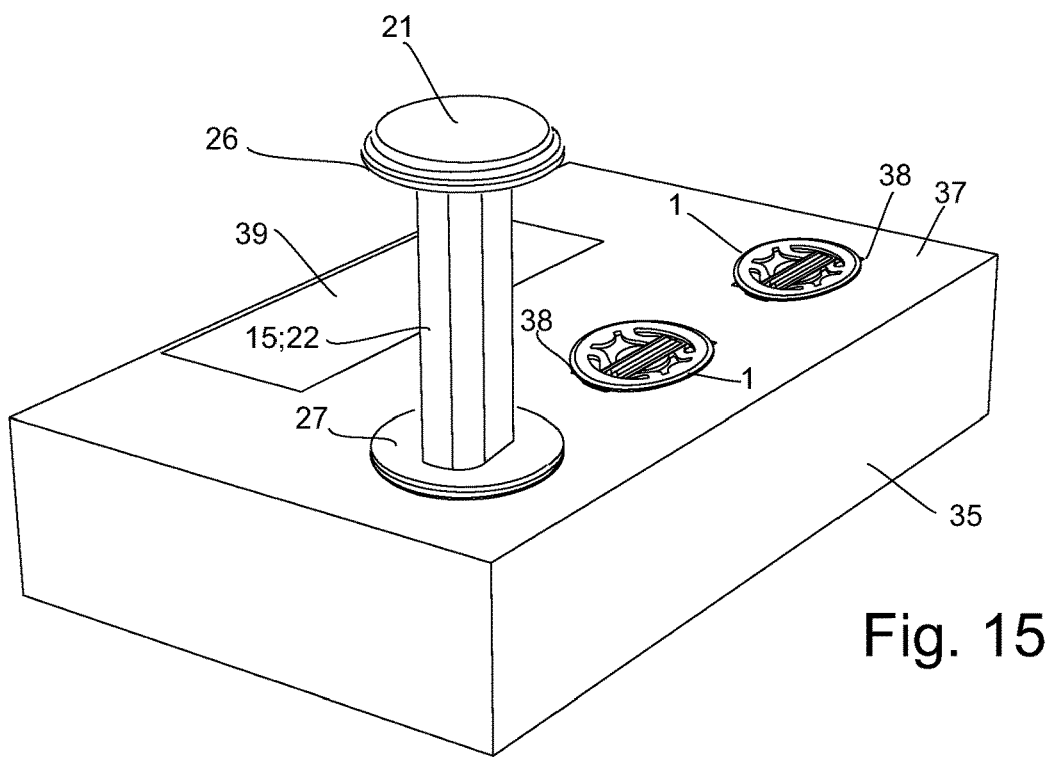
Figure 16:
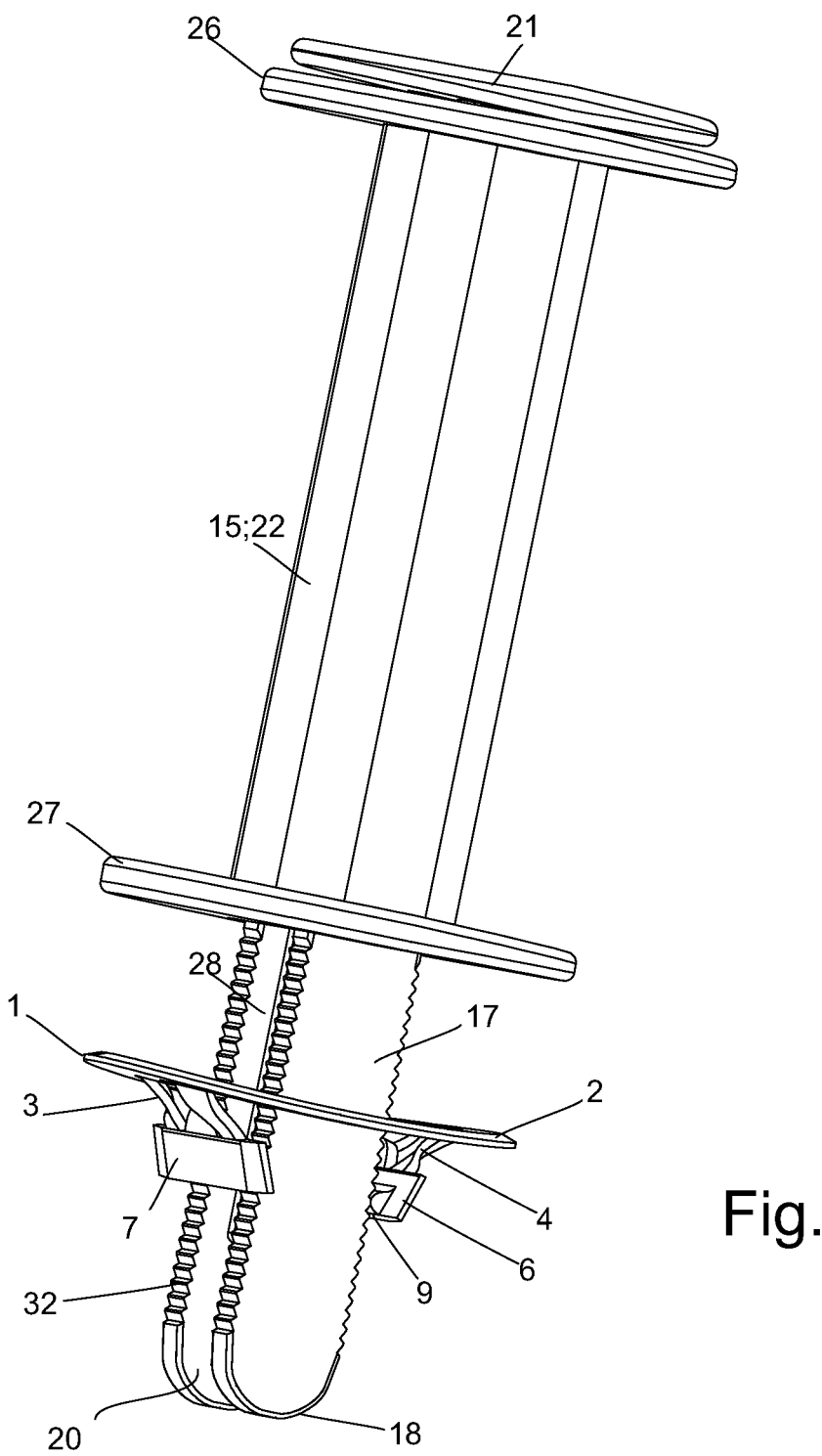
Figure 17:
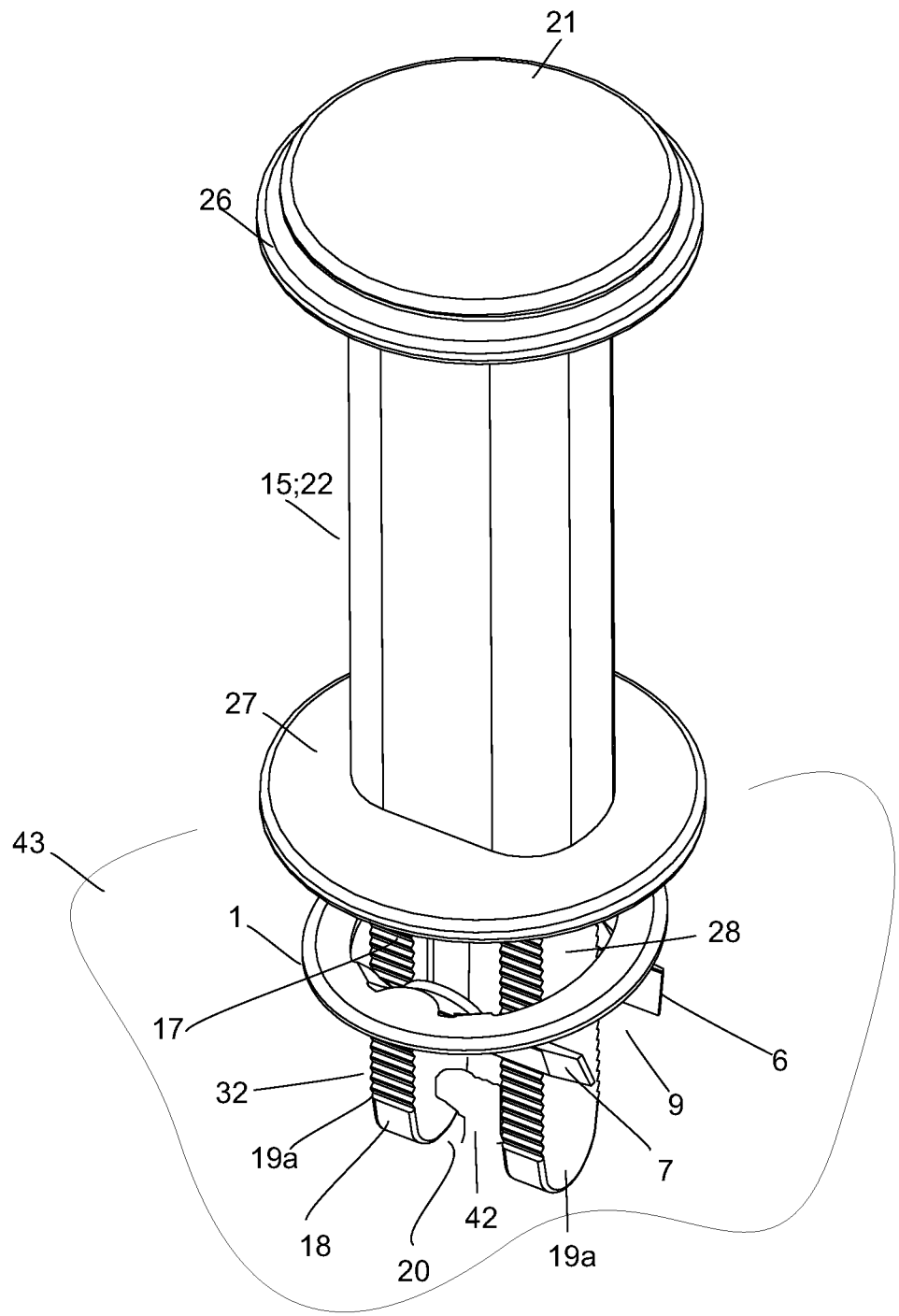
Figure 18:
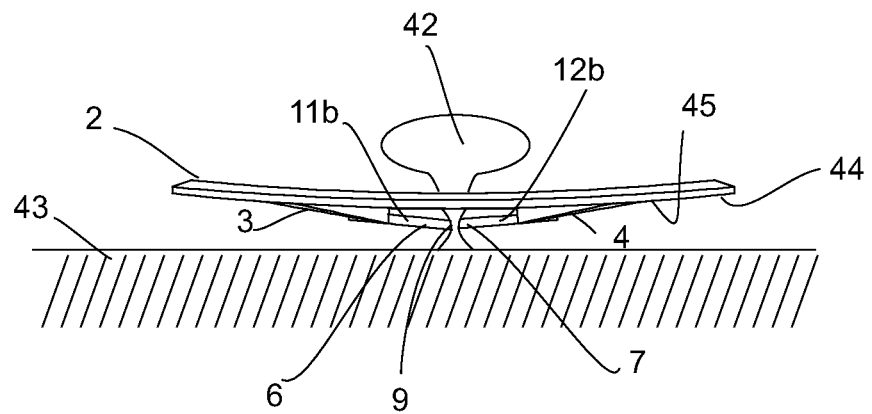
Figure 19:
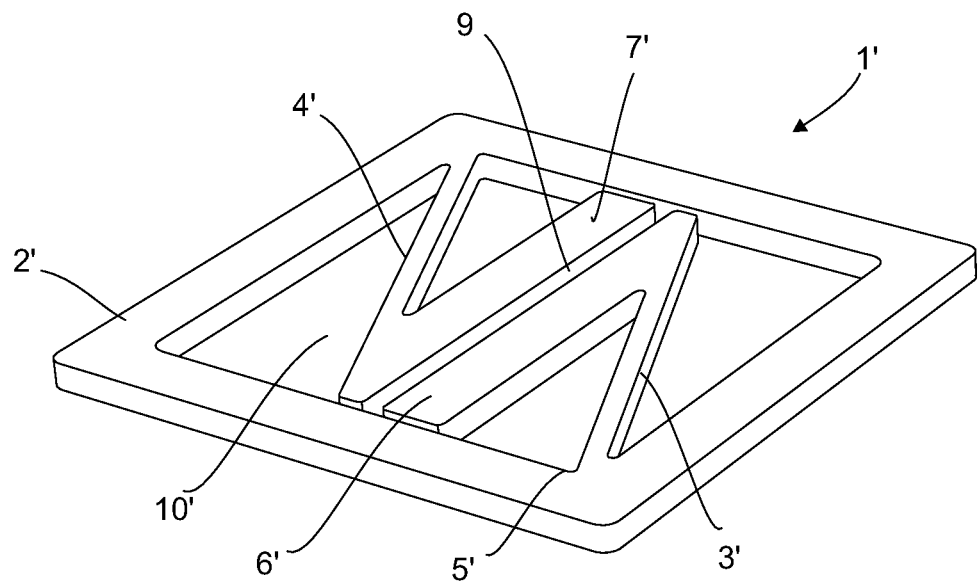
Figure 20:
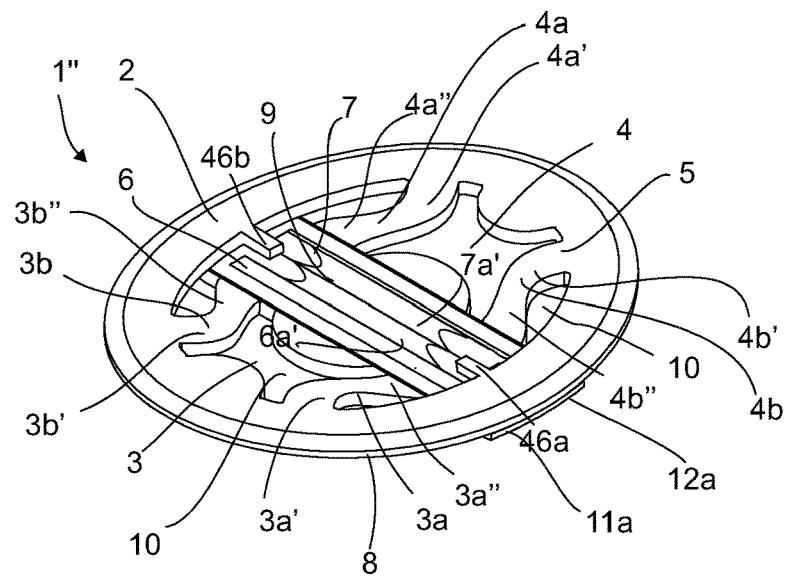
Figure 21:
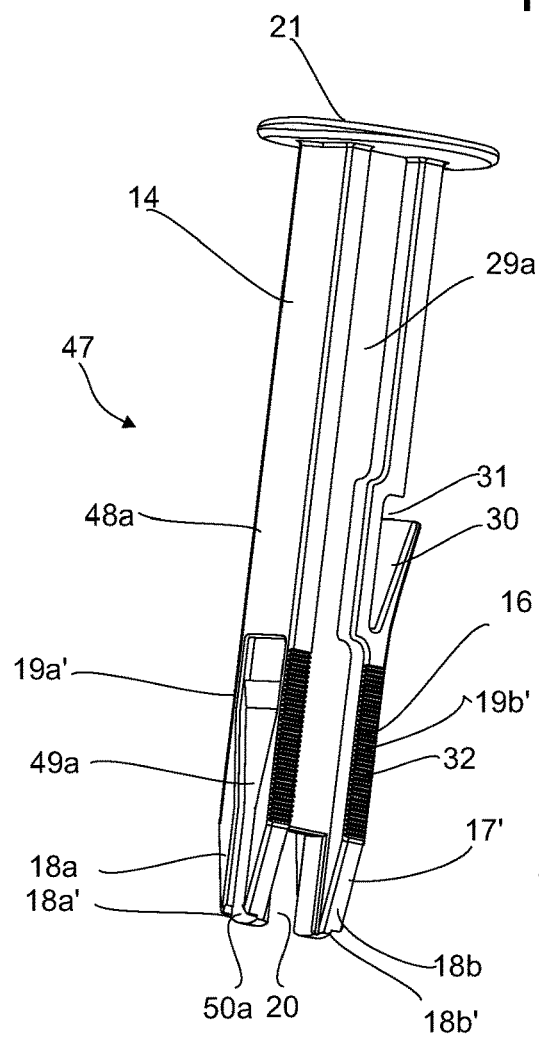
Figure 22:
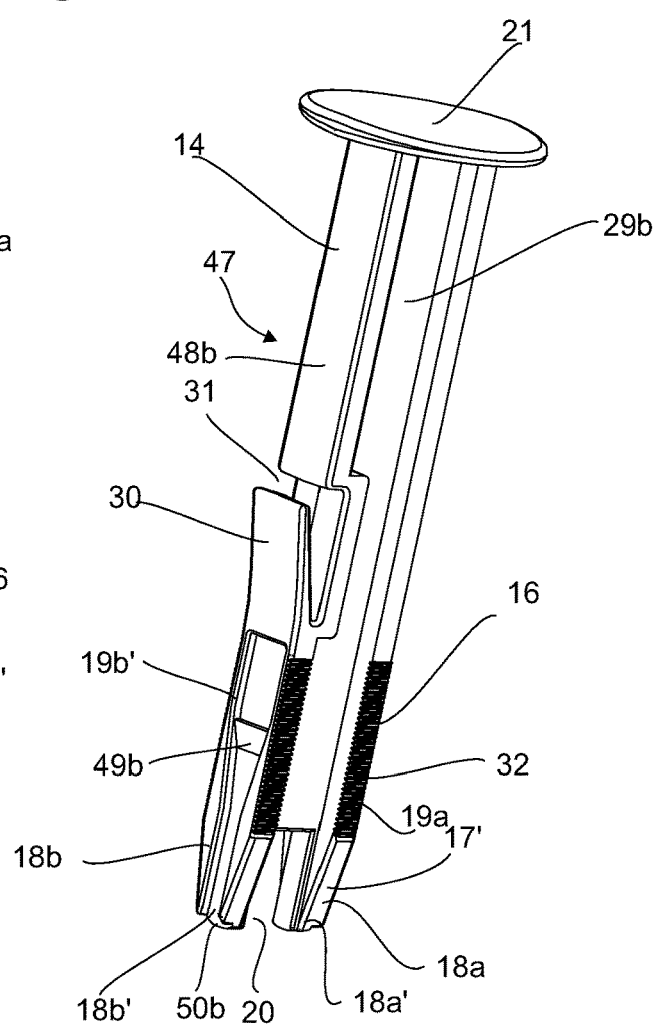
Figure 27:
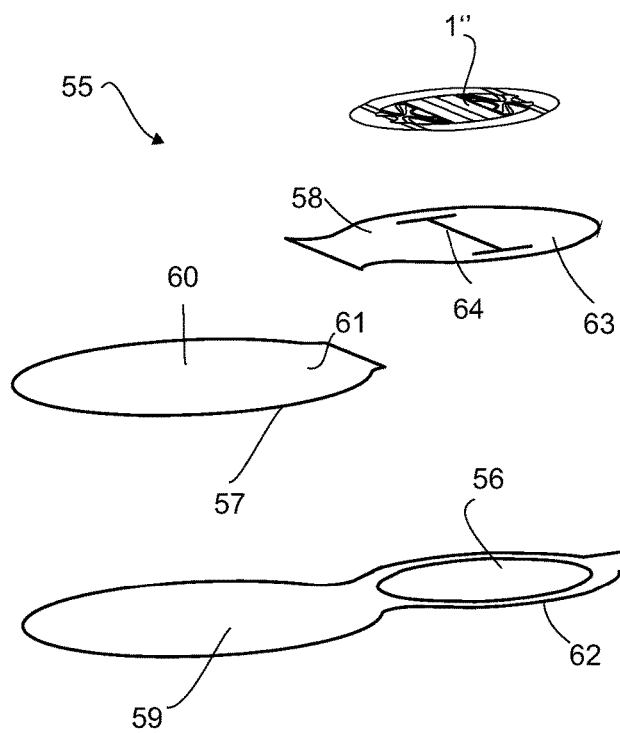
Figure 29:
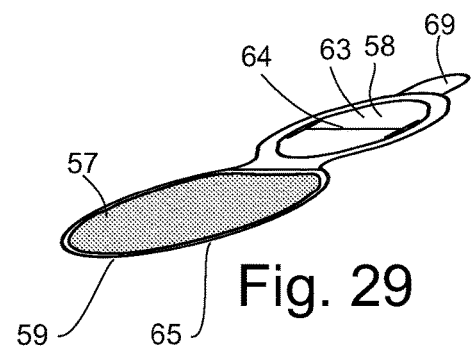
Figure 28:
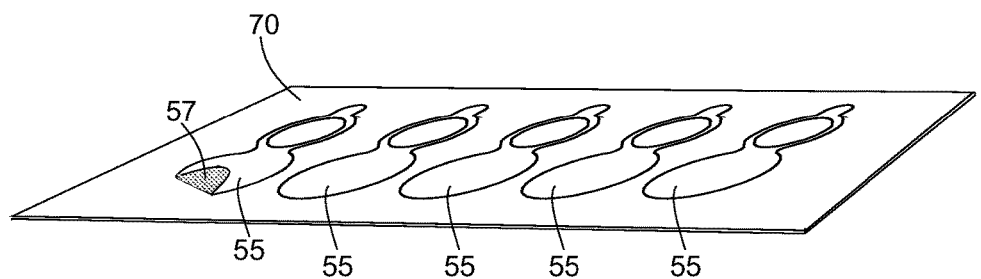
Figure 30:
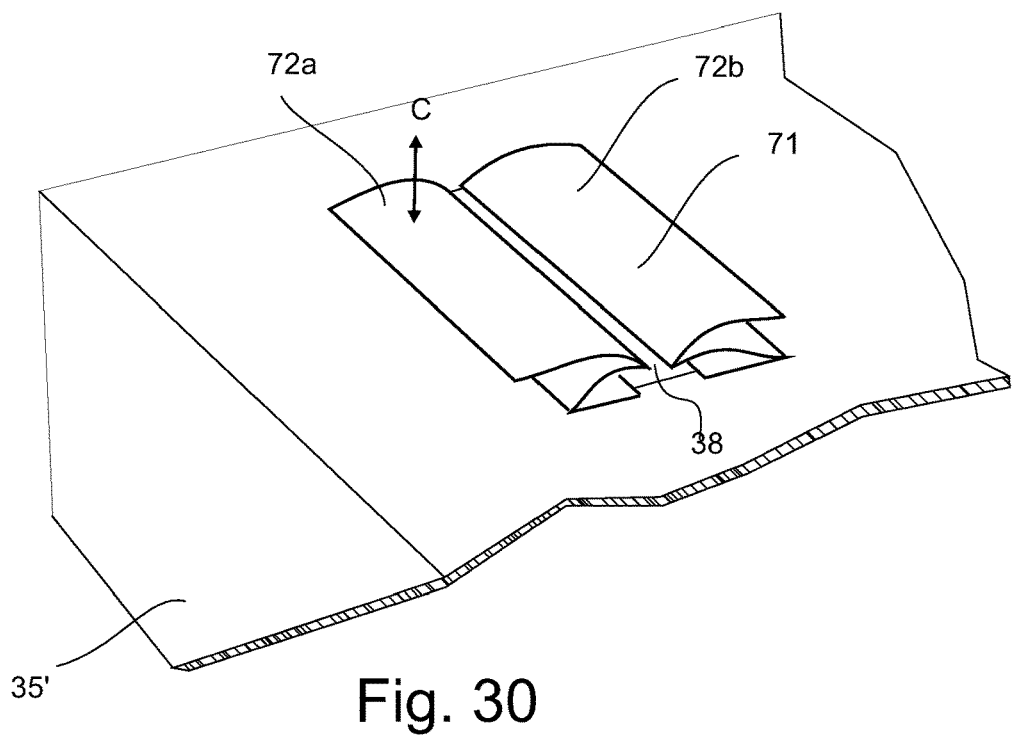
Figure 31:
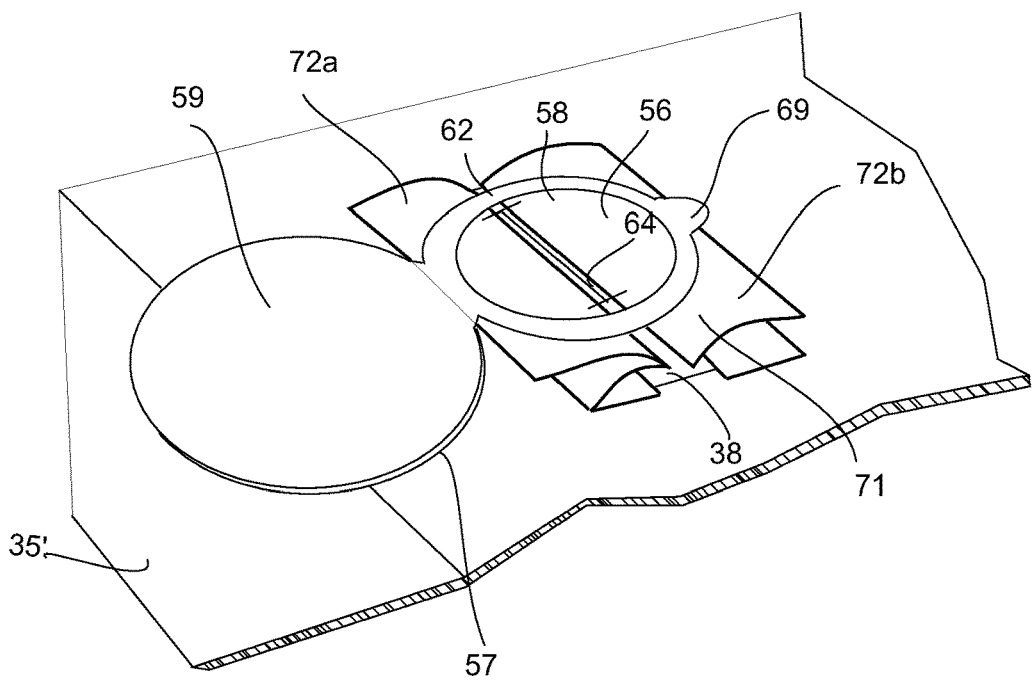
Figure 32:
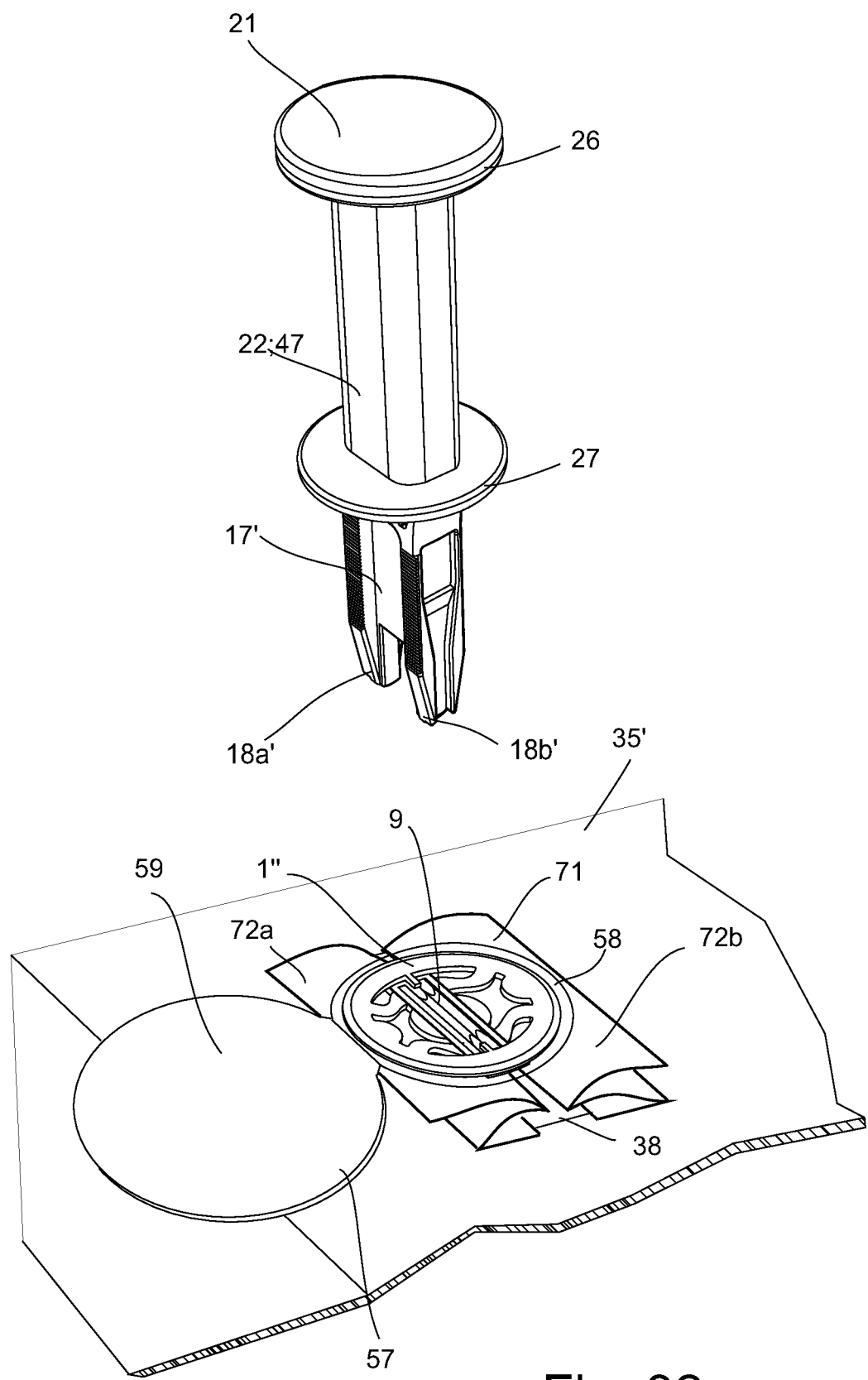
Figure 33:
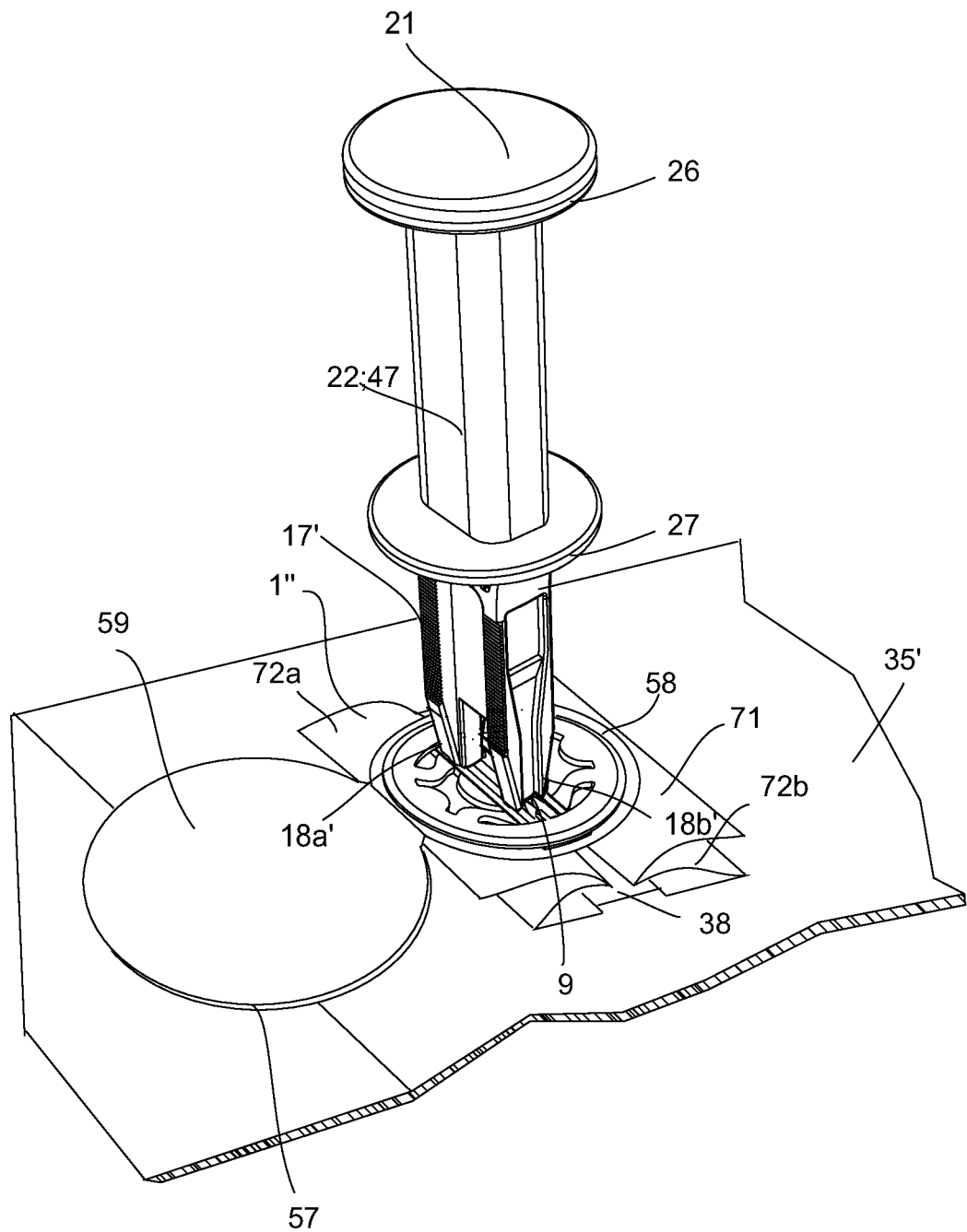
Figure 34:
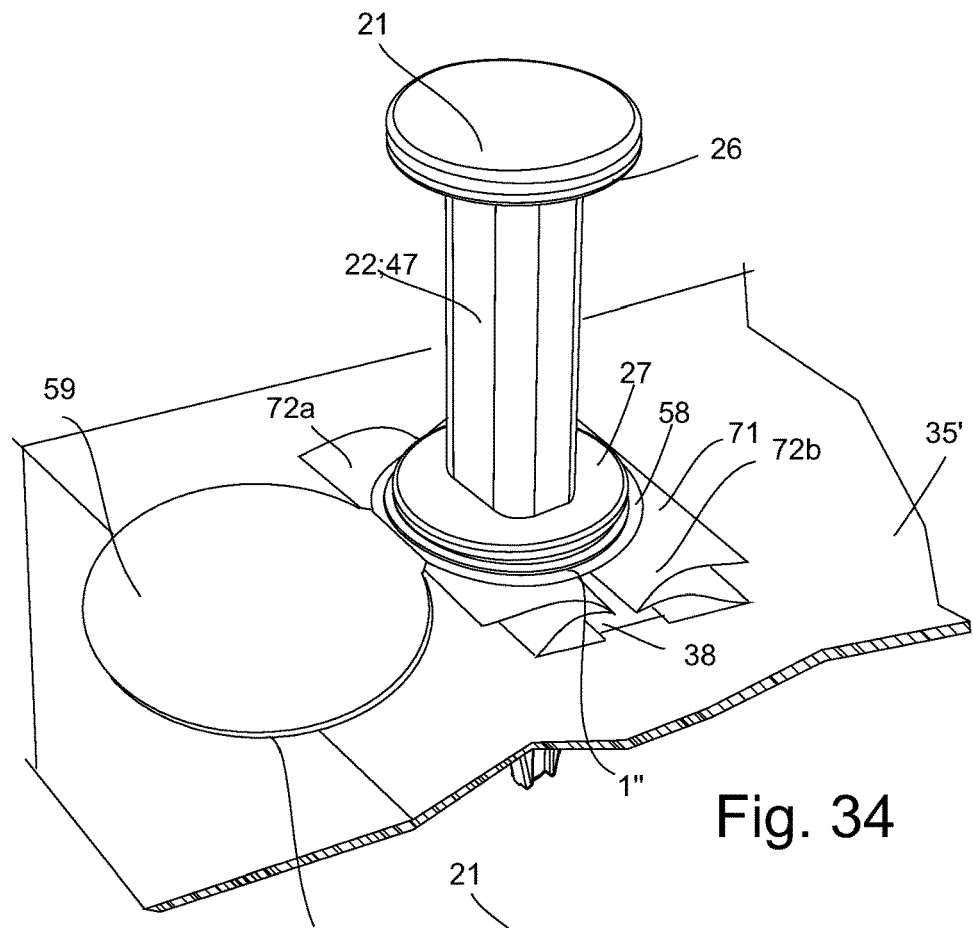
Figure 35:
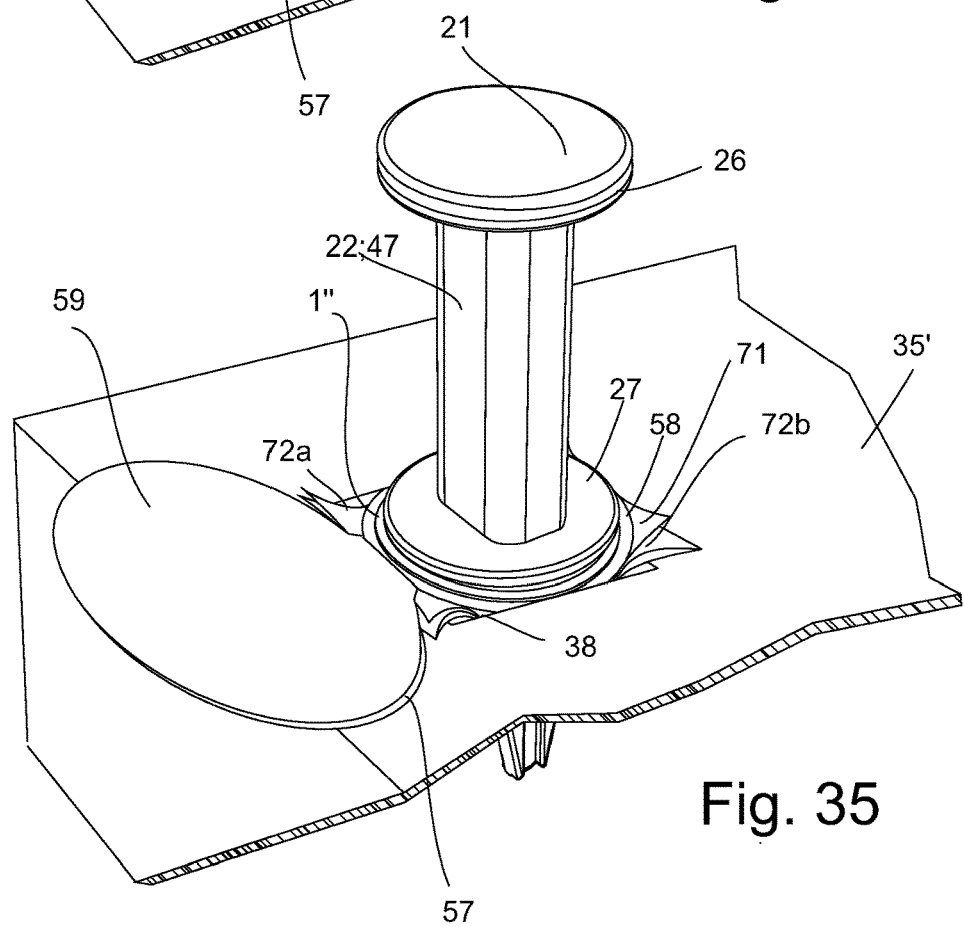
Figure 36:
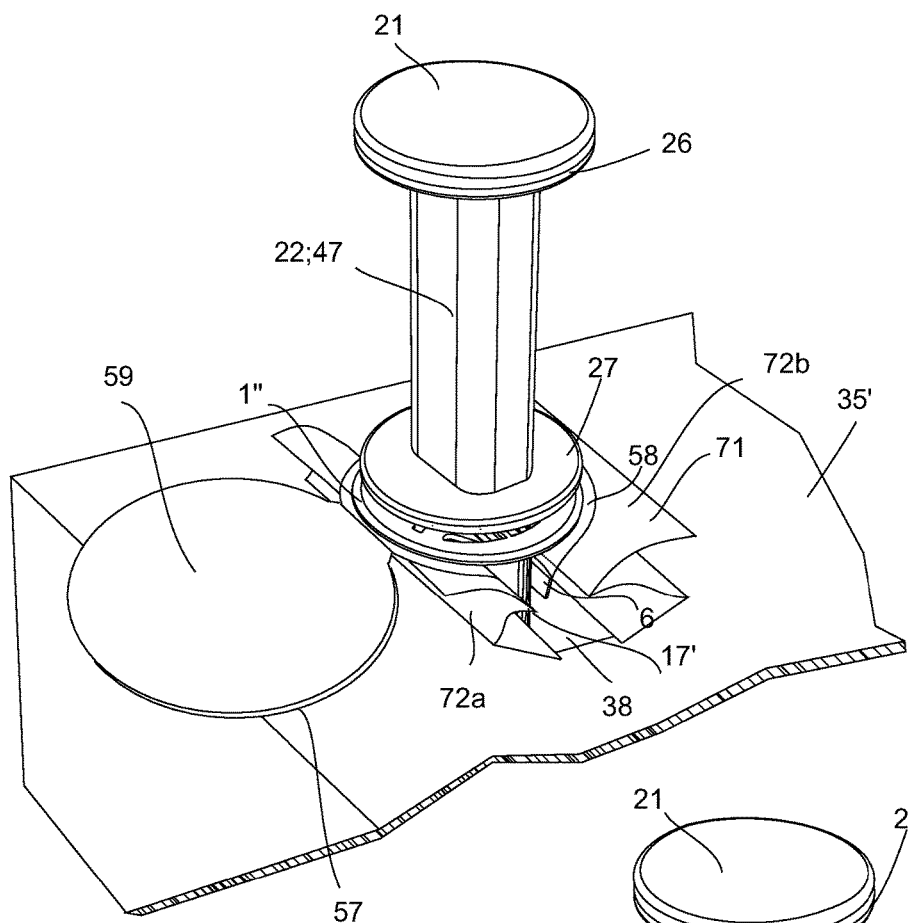
Figure 37:
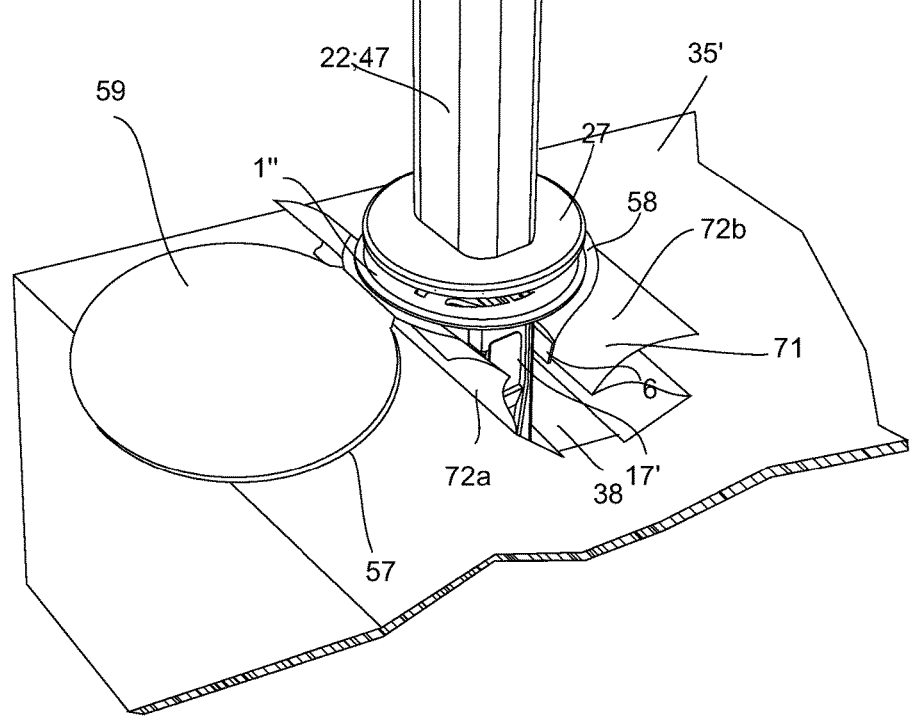
Figure 39:
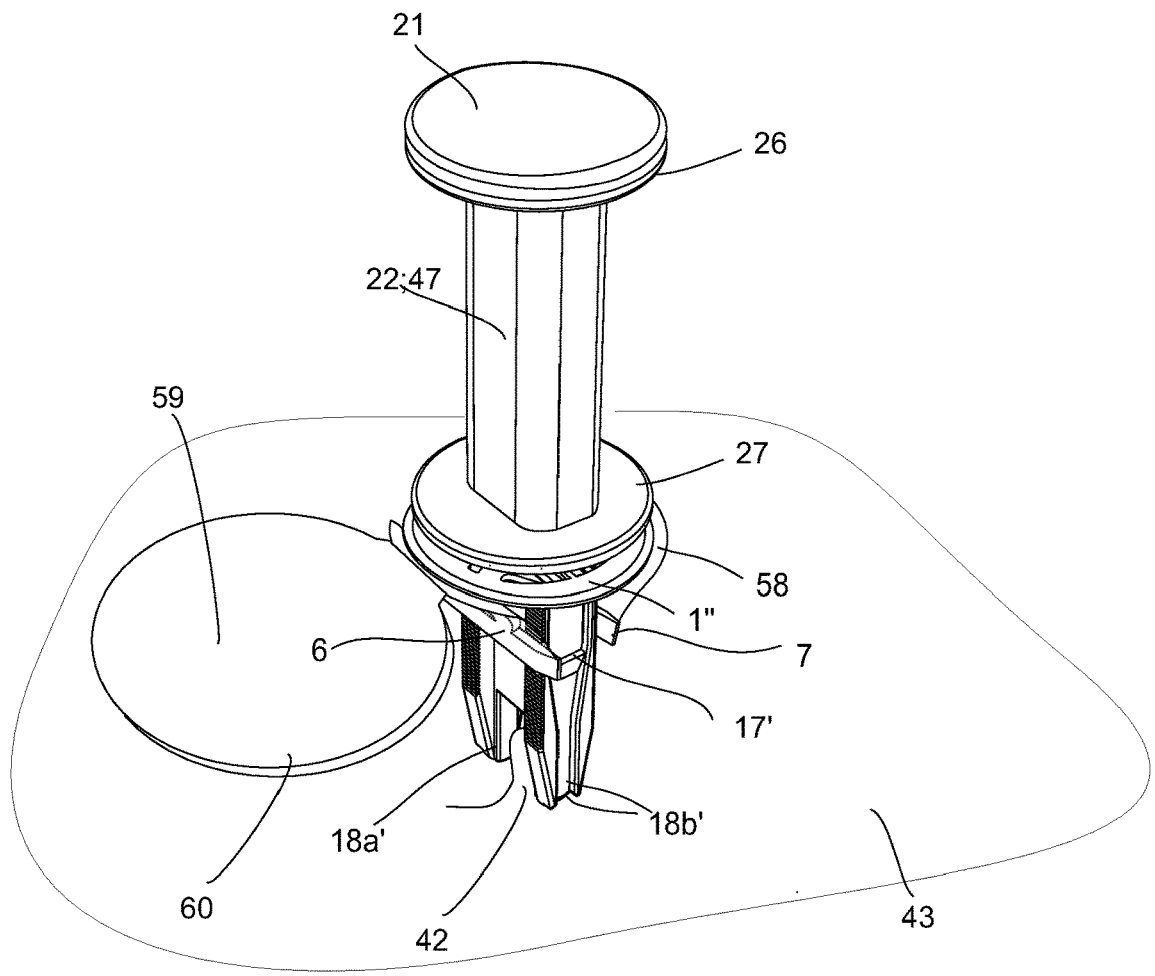
Figure 40:
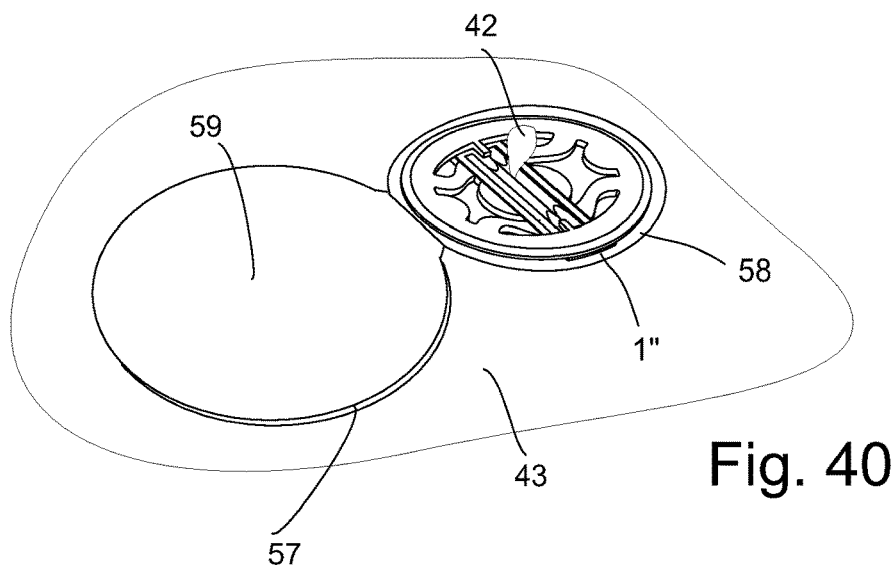
Figure 41:
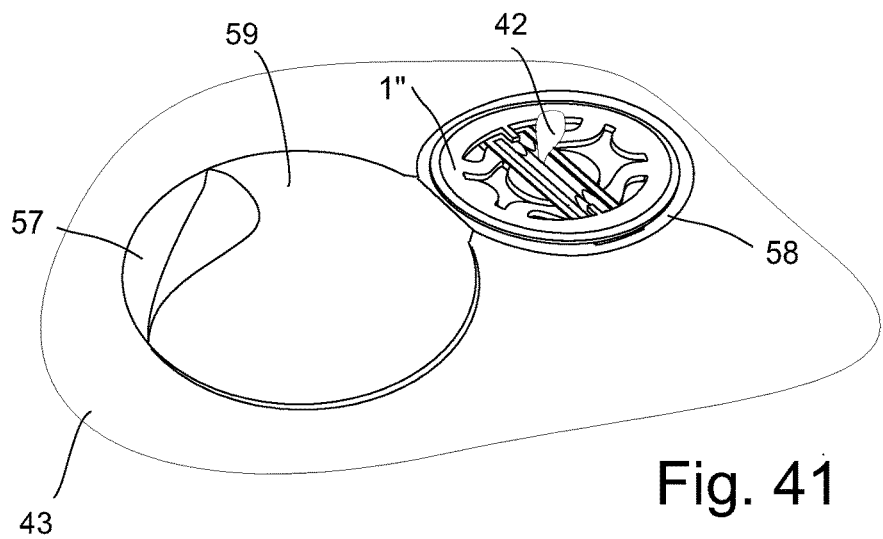
Figure 42:
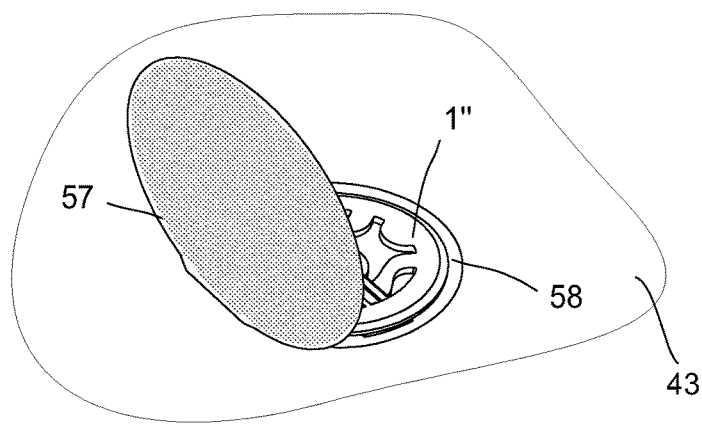
Figure 43:
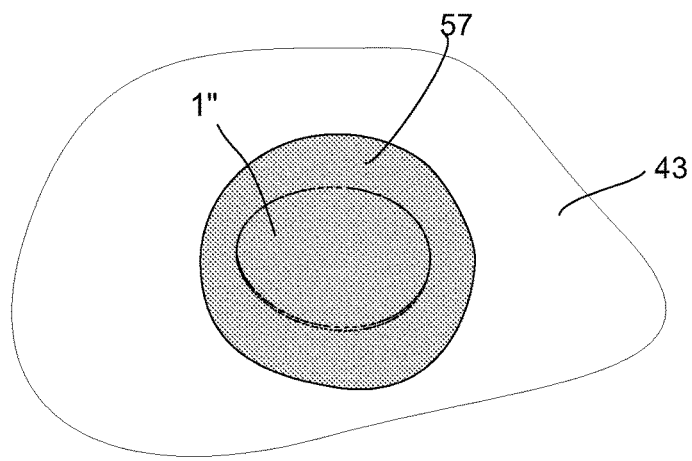

FIG. 1 shows a first embodiment of a skin tag removing device seen from the applicator-facing topside, in a ready-to-use position, wherein the occlusion members have been loaded and biased below the base member to be pre-tensioned, FIG. 2 is a side view of the same, FIG. 3a is a perspective view of the same, FIG. 3b shows the first embodiment of a skin tag removing device in a "straight-from the-mold" condition prior to being pre-tensioned into the "ready-to use-position" of FIGS. 1-3a, FIG. 4 is a perspective view of a first embodiment of an applicator rod of the applicator system, FIG. 5 is the same seen from the long side, FIG. 6 is a perspective view of a housing for an applicator rod, FIG. 7 is the same seen from the long side, FIG. 8 is a perspective view of a second embodiment of an applicator rod of the applicator system, FIG. 9 is the same seen from the long side, FIG. 10 is a longitudinal section taken along line X-X of a modification of the housing shown in FIG. 6, FIG. 11 is a perspective view of an exemplary first simple embodiment of a holder component seen from above, FIG. 12 is the same fitted with the first embodiment of a skin tag removing device, FIG. 13 is an enlarged scale view of the encircled fragment of the holder component of FIG. 12, FIG. 14 shows an applicator arranged ready to engaging the first embodiment of a skin tag removing device presented on the holder component seen in FIGS. 11 and 12, FIG. 15 shows operating the applicator system of the present invention wherein the applicator head of the applicator end is brought to engage the first embodiment of a skin tag removing device, FIG. 16 is an enlarged scale view of the first embodiment of a skin tag removing device clamped on the applicator head, FIG. 17 shows the applicator system according to the present invention wherein the first embodiment of a skin tag removing device is about to be mounted on a skin tag, FIG. 18 shows the first embodiment of a skin tag device occluding a skin tag, FIG. 19 shows a second embodiment of a skin tag removing device in form of a variant of a simple skin tag removing device having occlusion members that do not extend above the base member, FIG. 20 shows in perspective a third embodiment of a skin tag removing device seen from the applicator-facing topside, in a ready-to-use position, wherein the occlusion members have been loaded and biased below the base member to be pre-tensioned, FIGS. 21 and 22 are different perspective side views of a third embodiment of an applicator rod of the applicator system of the present invention, FIG. 23 shows the applicator rod from the first exterior free face opposite the second exterior free face that has the stopper, FIG. 24 shows the third embodiment of an applicator rod from the second exterior free face, FIG. 25 is an exploded plane view of the third embodiment of a skin tag removing device in an adhesive skin tag removing unit including a double-adhesive layer and an adhesive cover, FIG. 26 shows the same in assembled state from the applicator facing side, FIG. 27 shows the same in an enlarged exploded perspective view, FIG. 28 shows a protective release sheet with five skin tag removing units without skin tag removing devices, FIG. 29 shows the skin tag removing unit without skin tag removing device and from its skin-contacting face, FIG. 30 shows, in perspective, a fragment of an embodiment of a flexible release structure mounted at a hole of a modified holder component, FIG. 31 shows the same with the assembled skin tag removing unit,—without skin tag removing device—, releaseably mounted on the flexible release structure shown in FIG. 30 and ready for adhering a skin tag removing device, FIG. 32 shows the same now with a skin tag removing unit releaseably mounted on the flexible release structure shown in FIG. 30 and the third embodiment of an applicator rod ready for mounting the third embodiment of a skin tag removing device on its applicator head, FIG. 33 shows the same where the tapered end of the applicator head of the third embodiment of an applicator rod is positioned to penetrate the aperture of the third embodiment of a skin tag removing device included in a skin tag removing unit on a modified holder component with flexible release structure to open the occlusions members, FIG. 34 shows the same where the applicator head has been pressed towards the top wall of the modified holder component and the flexible release structure has been partly compacted, FIG. 35 shows the same where the applicator head has been pressed against the hole so that the opposite flexible release structure parts are pushed slightly into the hole of the modified holder component to initiate detachment of adhesive layer from said release structure part, FIG. 36 shows the same where the applicator is lifted slightly free of the top wall of the modified holder component, but where the adhesive layer, which is now best attached to the skin tag removing device, is still partly adhered to the flexible release structure parts, FIG. 37 shows the same where the applicator head is lifted further upwards from the top wall of the modified holder component and one of the release liner structure parts has detached more than the other release liner structure part, thus the mounting step just before the skin tag removing unit is completely released from the flexible release structure of the modified holder component, FIG. 38 shows the same where the third embodiment of a skin tag removing unit is now mounted on the applicator head of the third embodiment of an applicator rod, FIG. 39 shows the same with a skin tag arranged in the space of the tapered tip of the applicator head of the third embodiment of an applicator rod, FIG. 40 shows the skin tag removing unit squeezing a skin tag between the occlusion members after the applicator head of the third embodiment of an applicator rod has been withdrawn, FIG. 41 shows the skin tag removing unit on a skin tag with the large diameter release liner partly detached, FIG. 42 shows that the cover, relieved of the large diameter release liner, is being pivoted to cover the occluded skin tag, and FIG. 43 shows the skin tag removing device in its covered occluding position.

Although the skin tag removing device shown in FIGS. 1-3a,3b,20,25,26,27, and 32-43 has an oval or circular shape other shapes, such as any polygonal shape, are also contemplated within the scope of the present invention, as also illustrated in FIG. 19 of the second embodiment of a skin tag removing device. The shape of a skin tag removing device shown in PCT/IB2011/000265 is e.g. square.

FIGS. 1-3a,3b are described below in relation to a first embodiment of a skin tag removing device, which is ring-shaped. The oblong ring-shaped base member 2 may be seen as having a major axis X and a minor axis Y, and in the present exemplary embodiment the skin tag removing device is symmetrical about both axes X and Y. Such symmetry is not mandatory but has turned out to be a very efficient design and posses several manufacturing advantages, such as simple moulding and low manufacturing costs.

Two opposite flexible pressure members, a first pressure member 3 and a second pressure member 4, extend towards each other from the ring-shaped base member 2 along the major axis X.

Each pressure member 3,4 consist of two V-shaped pressure member parts 3a,3b and 4a,4b. Each respective V-shaped pressure member part 3a,3b;4a,4b has a first end of a respective first leg 3a',3b';4a'4b' secured to the edge 5 of the ring-shaped base member 2 along the interior diameter of said ring-shaped base member 2 so that opposite apices of the two sets of respective V-shaped pressure member parts 3a,3b and 4a,4b face each other. The second legs 3a",3b" and 4a" 4b" have respective second ends secured to elongate occlusion member 6 and 7, respectively, at a distance from each other about the minor axis Y. This distance is defined amongst other by the angle of the apex of the V-shaped pressure member part 3a,3b;4a,4b, the lengths of the first legs 3a',3b';4a'4b', the lengths of the second legs 3a",3b";4a"4b", and by the securing point of the ends of the legs to the edge 5 of the ring-shaped base member 2. The distance is further defined by the size of a central opening 10 of the ring-shaped base member 2, which ring-shaped base member 2 is sized to provide space for both pressure members 3,4 and occlusion members 6,7, and to allow the pivoting of same together.

The pressure members 3,4 are highly flexible and have an in-build memory making them able always to aim for returning to the most relaxed position close to the plane of the ring-shaped base member 2 after having been pivoted from the position seen in FIG. 3b through the plane of the base member, to achieve the position seen in FIGS. 1-3a. Each occlusion member 6,7 has a reinforcing member 6a,7a, respectively, and is attached to an associated pressure member 3,4, so that it can pivot together with its pressure member 3,4.

Each of the views of FIGS. 1-3a show a "ready-to-use" condition of the skin tag removing device 1. The "ready-to-use" condition is induced from the "straight-from-the mould" condition seen in FIG. 3b by pivoting the occlusion members 6,7 to the opposite side of the base member 2, as described further below. The "ready-to-use" condition is the condition of the applicator system prior to the applicator head of the applicator end being inserted in the aperture 9 of the skin tag removing device 1, as also will be described in further details below.

The elongated occlusion members 6,7 that are facing each other are substantially parallel with the minor axis Y. They are also longer than the interior minor diameter of the central opening 10 of the ring-shaped base member 2. The aperture 9 for inserting the skin tag to be removed is, in the "ready-to-use" condition, delimited by opposite occlusion members 6,7 and opposite sections or lengths of the perimeter of the edge 5 of the ring-shaped base member 2.

In the "ready-to-use" condition the flexible pressure members 3,4 and their associated occlusion members 6,7, are deflected slightly out of the plane of the ring-shaped base member 2 whereto their first legs 3a',3b';4a'4b' are secured to arrange the occlusion members 6,7 below said plane. The lengths of the occlusion members 6,7 are selected so that opposite free ends 11a,11b;12a,12b of each occlusion member 6,7 can be engaged at the underside 8 of the ring-shaped base member 2, thus at the skin-facing side. The occlusion members 6,7 become more or less pre-tensioned by being pivoted from the condition seen in FIG. 3b, in which the skin tag removing device comes straight from the mold with pressure members in relaxed, angled and protruding position from opposite the skin-facing side, to the pre-tensioned position seen in FIGS. 1-3a.

The more the occlusion members 6,7 subsequently are spread apart, e.g. when a component is inserted in the aperture 9 between the occlusion members so that the pressure members 3,4 are brought to pivot even further away from the "straight-from-the mold" condition, the higher tension of the pressure members 3,4. The pressure members 3,4 will now act as opposite spring members to return the occlusion members 6,7 to the most relaxed condition in the current situation whenever possible. In the "ready-to-use" condition the free ends 11a,12a;11b,12b of an occlusion member 6,7 engage the underside of the ring-shaped base member 2. The pivoting of the pressure members 3,4 accumulates energy that makes the pressure members 3,4 to return the occlusion members 6,7 towards the skin-facing underside of the base member 2.

When the skin tag removing device 1 of the first embodiment seen in e.g. FIGS. 1-3a;3b of the present invention leaves the moulding tool it is in a configuration seen in FIG. 3b wherein the pressure members 3,4 and associated occlusion members 6,7 are initially angled above the top side of the base member 2, thus away from the face of the base member to become the skin-contacting face. Subsequently the occlusion members 6,7 are moved below the underside 8 of the base member 2 in order to obtain a pre-tensioning of said pressure members 3,4 and occlusion members 6,7 of the skin tag removing device 1 which now has assumed the pre-tensioned "ready-to-use" condition seen in FIGS. 1-3*a*.

The angle of the pressure members 3,4 in relation to the plane of the base member before tensioning, thus as seen in FIG. 3*b*, can be about 45°, but can be any angle, which provides the intended level of pre-tensioning when the pressure members are pivoted. For said pre-tensioning the flexible pressure members 3,4 are thus forced to pivot about the securing points or hinges of the first legs 3*a'*,3*b'*;4*a'*4*b'* to the edge 5 of the ring-shaped base member 2. Once this applied tensioning force is removed counteraction takes automatically place to reassume the most relaxed condition of the flexible pressure members 3,4.

The design of the pressure members 6,7, having V-shaped opposite pressure members parts 3*a*,3*b*;4*a*,4*b* gives a pressure member 3,4 excellent spring properties. The V-shaped design is preferred although variants are within the scope of the present invention. For example the pressure members can simply be a spring member shaped as fingers spread as a fan, which fingers are secured to both the ring-shaped base member 2 and to an occlusion member 6,7. Yet an alternative design of a pressure member is a flap fitting inside the central opening 10 of the ring-shaped base member 2 and being hinged to the edge 5 of the ring-shaped base member 2 and having a free end provided with the elongate occlusion member 6,7.

The opposite elongate occlusion members 6,7 can be spaced apart to enlarge the aperture 9 so that the skin tag removing device 1 can pass over a skin tag, as illustrated in e.g. the subsequent FIGS. 17 and 39. Enlarging the aperture 9 is done by also increasing the mutual distance between the opposite elongate occlusion members 6,7, which action also increases the distance between the opposite elongate occlusion members 6,7, and the plane of the ring-shaped base member 2.

The oblong appearance of the ring-shaped base member 2 is very user-friendly. The user tends to grasp an object the easiest way, which will be where the object provides most and best space for operating it. In the present case this is along the major axis but in case of a circular skin tag removing device the aperture provides inherent instructions for grasping.

FIG. 4 is a perspective view of a first, simple embodiment of an applicator rod 13 of the applicator system of the present invention. FIG. 5 shows the same seen from the long side.

The first embodiment of the applicator rod 13 has an operating end 14 facing opposite a housing 15 and against an applicator end 16. The applicator end 16 has a bifurcated applicator head 17 that tapers towards a free tip 18. The bifurcated applicator head 17 is divided in opposite legs 19*a*,19*b* between which a space 20 sized and dimensioned for surrounding a skin tag (not shown) is delimited. The tapering of the applicator head 17 serves to facilitate inserting the applicator head 17 into the aperture 9 of the skin tag removing device 1. Opposite the applicator head 17 the operating end 14 is provided with an enlarged finger press button 21.

FIG. 6 is a perspective view of a first embodiment of a housing 15, and FIG. 7 shows the same seen from the long side. The housing 15 has a guideway 23 with an inlet 24 and an outlet 25. An inlet flange 26 is provided to surround the inlet 24 and has a larger area than said inlet 24. An outlet flange 27 is provided to surround the outlet 25 and has a larger area than said outlet 25. This reel design is very convenient to grasp. The cross-section of the guideway 23 is rectangular to receive a mating applicator rod in a reciprocating and simple manner. The cross-section of the first embodiment of an applicator rod 13 is thus also rectangular and the applicator rod cannot rotate in the guideway.

FIG. 8 is a perspective view of a second embodiment of an applicator rod 28 of the applicator system, and FIG. 9 is the same seen from the long side.

The second embodiment of the applicator rod 28 corresponds substantially to the first embodiment 13 and for like parts same reference numerals are used. The second embodiment 28 differs from the first embodiment 13 in that the applicator rod 28 has a first guide groove 29 along at least a part of its length. The first guide groove 29 can be provided on just one longitudinal side or on both longitudinal sides, along the entire length or just on a part of the length. The first guide groove 29 gives the applicator rod 13*a* U-shaped or I-shaped cross-section.

For optimum fit and sliding into the guideway 23 of the housing said guideway 23 should the best have a corresponding cross-section sized to reciprocate the applicator rod 13;28.

The applicator rod has a second stopper 30 in form of an axially extending leaf spring 30 that can flex into an axially extending recess 31 of the applicator rod 28. Said applicator rod 28 reciprocates inside a guideway 23 of a second embodiment of a housing 22 seen in longitudinal section in FIG. 10.

The second embodiment of a housing 22 has an exterior appearance similar to the first embodiment of a housing 15 seen in FIG. 6, as well as a rectangular cross-section of the guideway 23 to receive the rectangular cross-section of the applicator rod 28, and for like parts same reference numerals are used.

The second embodiment of a housing 22 further has a first stopper 33 in form of a breast 34 that catches the second stopper 30, the leaf spring, when the applicator head 17 is returning towards the inlet 24 of the guideway 23, thereby preventing separation of applicator rod 28 and housing 22. Thus the second embodiment of an applicator rod 28 cannot be pulled out of the second embodiment of the housing 22.

The exterior surface of the applicator head 17 has ridges 32 to improve engagement with the opposite occlusion members 6,7 of a skin tag removing device 1.

FIG. 11 illustrates an exemplary embodiment of a first embodiment of a holder component 35 formed as a box 36. The rectangular box 36 has a top wall 37 that constitutes the mounting surface with holes 38, in the present embodiment three holes 38, each sized for carrying a skin tag removing device 1, e.g. the first embodiment of a skin tag removing device 1, in the "ready-to-use" condition, as shown in FIG. 12. The box 36 further has a compartment 39 for storing e.g. the applicator (not shown) and/or extra skin tag removing devices when not in use. The compartment 39 is not mandatory in that the applicator quite as well can be stored separately.

The holes 38 are rectangular so that the first embodiment of a skin tag removing devices 1 rests on the mounting surface of the top wall 37 with the opposite occlusion members 6,7, free to pass through the holes 38, as seen better in the enlarged scale view of FIG. 13 showing the encircled fragment of the box 36 of FIG. 12. The hole 38 is thus fitted with a first embodiment of a skin tag removing device 1 and the occlusion members 6,7 are ready to be spread apart below the top wall 37. The opposite parts of the ring-shaped base member 2 along the major axis X rest on the mounting surface of the top wall 37 partly on the mounting surface along the perimeter of the hole 38 crosswise along the shortest side of the hole 38. The longer sides of the hole 38 provide free access for pivoting the pressure members 3,4 into a further increased tensioning angle by moving the occlusion members 6,7 below the top wall 37 into a free space 40 below said top wall 37.

A skin tag removing device of the present invention may advantageously have an adhesive (not shown) at the underside, the skin-contacting surface, opposite the topside, which adhesive can be utilized to both secure the correct position of the skin tag removing device 1 in relation to the hole 38, and to secure the skin tag removing device on the skin around the skin tag after completed application and mounting of the skin tag removing device.

The box 36 has a circumferential wall 41, the height of which defines the depth of the free space 40 below the top wall 37. The circumferential wall 41, and thus the box 36, may advantageously be placed on a support face (not shown). To facilitate removal of an adhering skin tag removing device 1 from the box 36 the top wall 41 may expediently have a first release liner at the area in contact with the skin tag removing device to provide for easy detachment and release of the skin tag removing device.

A skin tag removing device may be provided with a detachable adhesive cover (not shown) when positioned on the box 1. The detachable cover can utilize the same release liner or another release liner for said cover to provide easy access for the applicator. The same cover can be reused to cover and enclose the skin tag once the skin tag removing device has been mounted on the skin tag.

The adhesive and/or the cover is a further means to prevent the correctly mounted skin tag removing device from entangling or being caught by exterior items, such as e.g. the clothes. The adhesive on the underside and/or covers may then also serve to prevent accidental non-timely tearing-off of the skin tag removing device.

FIG. 14 shows the first step of operating the aforesaid first embodiment and second embodiment of an applicator systems 1,1',1";13,28,47;15,22 of the present invention without a flexible release structure, which will be described later. Although the applicator system shown for the operating method in the subsequent FIGS. 14-17 includes the second embodiment of the housing 22 and the second embodiment of the applicator rod this shall not be construed as limiting the present invention. The applicator system can within the scope of the present invention comprise any of the first, second and third embodiments of the applicator rods 13,28, 47 and housings 15,22, which third embodiment 47 of an applicator rod will be described more fully in the subsequent figures.

In FIG. 14 the second embodiment of an applicator rod 28 and the second embodiment of a housing 22 are arranged in the position wherein the applicator head 17 is ready to be brought to engage a skin tag removing device 1 according to the first embodiment on a box-shaped 36 holder component 35.

The second embodiment of housing 22 is in its position farthest from the applicator head 17 and abut the finger pressing button 21, this way exposing the applicator end 16 and the ridges 32 to be free to be inserted into the aperture 9 of the first embodiment of the skin tag removing device 1 in the step of operating the applicator system of the present invention, as shown in FIG. 15.

In the position shown in FIG. 15 the applicator head 17 of the applicator end 16 of the second embodiment of applicator rod 28 is brought to engage the first embodiment of the skin tag removing device 1. The applicator head 17 of the applicator end 16 is simply forced through the aperture 9 of the first embodiment of skin tag removing device 1 whereby the ridges 32 engage the occlusion members 7,8. The mutual positions of the second embodiment of the applicator rod 28 and the second embodiment of the housing 22 are the same as in the position shown in FIG. 14. The second embodiment of the applicator rod 28 and the second embodiment of the housing 22 are moved together in the direction indicated by arrow A, as one combined unit without axial displacement of applicator rod and housing in relation to each other when the engagement shown in FIG. 15 takes place. This position can e.g. be when the outlet flange 27 of the second embodiment of the housing 22 meets or is close to the ring-shaped base member 2 of the first embodiment of the skin tag removing device 1, but this position can be any position in which a firm, reliable engagement of any of the skin tag removing devices and applicator heads of applicator rods of the present invention is possible.

In the enlarged scale view of FIG. 16 the applicator 22,28 and the engaging first embodiment of a skin tag removing device 1 have been moved away from the box 36 by retracting as one combined unit in the direction indicated by arrow B of FIG. 14. Combined removal of skin tag removing device and applicator from the box 36 can take place because the occlusion members 6,7 clamp well around the applicator head 17 of the applicator rod 28. The ridges 32 help to keep the first embodiment of a skin tag removing device 1 engaged until it is ejected from the applicator head 17.

As seen in FIG. 17, in order to apply the first embodiment of a skin tag removing device 1 on a skin tag 42, the applicator, which is fitted with a skin tag removing device as seen in FIG. 16, first has a skin tag 42 disposed in the space 20 between the legs 19a,19b of the applicator head 17 of the applicator end 16 of the applicator rod 28.

Then, the second embodiment of housing 22 is simply moved towards base member 2 of the skin tag removing device whereby the outlet flange 27 is expediently used to move the first embodiment of a skin tag removing device 1 in front of said outlet flange 27 thereby pushing the first embodiment of a skin tag removing device 1 towards the tip 18 of the applicator rod 28, which is resting on the skin surface 43, wherefrom the skin tag 42 protrudes. When the first embodiment of a skin tag removing device 1 reaches the skin surface 43, the first embodiment of a skin tag removing device 1 disengages the applicator head 17 and occludes with the occlusion members 6,7 around the skin tag 42, as seen in FIG. 18. Immediate upon disengagement the tensioning of the pressure members 3,4 make them try to get back to a more relaxed and not tensioned condition, which condition is when the occlusion members 6,7 meet the pedicle of the skin tag 42, or other transition to the skin surface. At least a part of the skin-contacting face 44, the underside of at least the base member 2 may, as mentioned above, has an adhesive 45 for adhering a skin tag removing device 1 to the skin 43.

The skin tag removing device described above in relation to FIGS. 1-16 is the first embodiment 1, however it can easily be replaced with any of the second and third embodiments of skin tag removing devices described below and be used with any of the applicator rods and housings disclosed herein.

FIG. 19 shows a second embodiment of a skin tag removing device of the present invention in for of a variant of a simple skin tag removing device 1' having occlusion members 6',7' that do not extend above or below the substantially square base member 2'. This second embodiment of a skin tag removing device 1' is of the kind known from e.g. PCT/IB2011/000265 and can be used with any of the applicators described above.

The pressure members 3'4' are flexible rods spanning the central opening 10' of the square base members 2' by having one end secured at a corner of the square base member 2' at the edge 5', and having an opposite end secured to the end of an associated elongate occlusion member 6',7' that diverges at an angle from said corner towards the subtending side of the base member 2' to define the aperture 9 for receiving a skin tag in the operative condition, similarly as described above in relation to FIG. 17.

A third embodiment of a skin tag removing device 1" is shown in FIG. 20 as a modification of the first embodiment of the skin tag removing device 1 shown in FIGS. 1-3b. The third embodiment of a skin tag removing device 1" is shown in a perspective view similar to the perspective view of FIG. 3a.

The modified skin tag removing device 1" corresponds substantially to the skin tag removing device 1 shown in FIGS. 1-3b, and for like parts same reference numerals are used. The modified skin tag removing device 1" shown in FIGS. 1-3b is also seen from the applicator-facing topside, in a ready-to-use position, wherein the occlusion members 6,7 have been loaded and biased below the base member 2 to be pre-tensioned ready for passing an applicator head through the aperture 9.

The modified skin tag removing device 1" of the third embodiment differs from the first embodiment of a skin tag removing device 1 in that the reinforcing members 6a',7a' of the respective occlusion member 6,7 are shorter, to provide space for two opposite guide beads or guide keys 46a,46b that protrude towards each other inside the central opening 10 from the interior diameter of the ring-shaped base member 2 above the aperture 9.

The modified skin tag removing device 1" is to be used in a modified applicator system utilising a third embodiment of an applicator rod 47 in form of the modified applicator rod shown in FIGS. 21-24. The third embodiment of an applicator rod 47 corresponds substantially to the second embodiment of an applicator rod 28 shown in FIGS. 8 and 9, and for like parts same reference numerals are used. The modified applicator rod 47 is operative with e.g. the second embodiment of a housing 22 shown in FIG. 10 but can also be used with the first embodiment of the housing 15, shown in FIGS. 6 and 7.

Just as the second embodiment of an applicator rod 28 the third embodiment of an applicator rod 47 has opposite first guide grooves 29a,29b along its length, or along at least a part of its length, and ridges 32 on the exterior surface of the modified applicator head 17' on respective opposite sides of the first guide grooves 29a,29b, which ridges 32 serve to engage the opposite occlusion members 6,7 of e.g. the third embodiment of a skin tag removing device 1" shown in FIG. 20, so that a temporary lengthwise position of the third embodiment of the skin tag removing device 1" can be maintained on the applicator head 17' prior to application of the third embodiment the skin tag removing device 1" on a skin tag, as e.g. shown in FIG. 17.

The modified applicator rod 47 thus is a third embodiment of an applicator rod, which differs a.o. from the second embodiment of an applicator rod 28 in that the respective opposite legs 19a',19b' of the applicator head 17' has respective tapered free tips 18a',18b' as in the first embodiment of an applicator rod 13 instead of rounded as in the second embodiment of an applicator rod 28 to better penetrate the aperture 9 of any of the embodiments of skin tag removing device 1,1',1" and open the occlusion members 6,7 for receiving the skin tag.

The opposite exterior free faces 48a,48b of the legs 19a',19b' of the applicator head 17', thus exterior to the space 20, is provided with second guide grooves 49a,49b inside which the guide beads or guide keys 46a,46b of the third embodiment of the skin tag removing device 1" runs when the applicator head 17' is inserted through the aperture 9 of the third embodiment of said skin tag removing device 1". The guide beads or guide keys 46a,46b serve for improved control and guidance of the position and orientation of the third embodiment of the skin tag removing device 1" both when being mounted on the applicator head 17', along the method steps shown in FIGS. 14 and 15, and when being ejected from said applicator head 17' by moving e.g. the second embodiment of a housing 22 down towards the skin with the third embodiment of the skin tag removing device 1" in front of the circumferential outlet flange 27.

FIG. 23 shows the third embodiment of an applicator rod 47 from the first exterior free face 48a opposite the second exterior free face 48b, which second exterior free face 48b in the present exemplary embodiment is the exterior free face including the stopper 30, as shown in FIG. 24. The first second guide grooves 49a has a first key opening 50a located at the tapered first free tip 18a' of the first tapered free tip part 18a, and the second second guide groove 49b has a second key opening 50b located at the tapered second free tip 18b' of the opposite respective second tapered free tip part 18b, between which free tapered tip parts 18a,18b the space 20 is delimited.

The side view of FIG. 23 shows that the first second guide groove 49a has the first key opening 50a at a first distal elongate guide groove section 51a, in the present case of substantially uniform width. Opposite the first key opening 50a the first distal elongate guide groove section 51a extends into a first intermediate guide groove section 52a that has a width that increases towards a first blind proximal elongate guide groove section 53a. A first shoulder 54a is located in the first blind proximal elongate guide groove section 53a of the first second guide groove 49a. The first shoulder 54a protrudes from the first second guide groove 49a to serve as a first temporary retainer for the inserted first guide key 46a or second guide key 46b of the third embodiment of a skin tag removing device 1" that has been arranged on the applicator head 17', e.g. using the method steps of the present invention, e.g. the method described in relation to subsequent FIGS. 30-40 as described below.

FIG. 24 shows the third embodiment of an applicator rod 47 from the second exterior free face 48b which is located opposite the first exterior free face 48a. The side view of FIG. 24 shows that from the second key opening 50b the second second guide groove 49b has a second distal elongate guide groove section 51b, in the present case of substantially uniform width. The second distal elongate guide groove section 51b extends into a second intermediate guide groove section 52b that has a width that increases towards a second blind proximal elongate guide groove section 53b. A second shoulder 54b is located in the second intermediate guide groove section 52b of the second guide groove 49b so that the second shoulder 54b protrudes from the second second guide groove 49b to serve as a second temporary retainer for the inserted first guide key 46a or second guide key 46b of the third embodiment of a skin tag removing device 1".

Thus the mounting method is not dependent on how the applicator head 17' is turned in relation to which guide key 46a,46b that face which shoulder 54a,54b. For example can the first guide face any of the first or second shoulder during inserting the applicator head 17' into the aperture 9 to spread the occlusion members 6,7 apart.

In the present third embodiment of an applicator rod 47 the first shoulder 54a and the second shoulder 54b are offset lengthwise along the longitudinal axis of the third embodiment of the applicator rod 47 so that axial disengagement of guide keys 46a,46b and co-operative shoulders 54a,54b on opposite sides of the aperture 9 takes place at different point of time during a releasing step from a modified holder component 35', in which releasing step the third embodiment of a skin tag removing device 1" is gradually set free from said modified holder component 35' when the applicator head 17' with engaged third embodiment of a skin tag removing device 1" is moved upwards and away from said modified holder component 35' and out of the hole 38, as described below in connection with FIGS. 36-38.

Emphasis is made that neither shoulders nor offset shoulders are mandatory. Accordingly, both shoulders 54a,54b can be provided in the same section of the respective second guide grooves 49a,49b, be provided at different sections or even be avoided. The axial distance between the shoulders 54a,54b influences on when the third embodiment of the skin tag removing device 1" is allowed to slide axially on the applicator head 17', and to which extent in response to a force directed away from the modified holder component 35', including when the adhesive force between modified holder component 35' and the adhesive skin-facing side of the third embodiment of the skin tag removing device 35', which skin-facing side is also the modified holder component facing side, is overcomed or is being overcomed.

The sliding engagement between guide keys 46a,46b and cooperative shoulders 54a,54b serve as a means to keep the third embodiment of the skin tag removing device 1" on the applicator head 17' when the skin tag removing device 1" is lifted free of its adhesive attachment to the modified holder component 35', e.g. any of the boxes 36,36', and to control this detachment and ensure that detachment is conducted smoothly and easily. In particular for the offset shoulders 54a,54b provided in the exemplary embodiment in relation to FIGS. 21-24, to make the detachment of the skin tag removing device from the holder component 35,35' happen at different times, and at different force at opposite exterior free faces 48a,48b, due to the engagement between shoulder 54a,54b and guide key 46a,46b also happens at different time during axial upwards displacement of the third embodiment of a skin tag removing device 1" on the applicator head 17' from the modified holder component 35'. Thus the distance between the shoulders 54a,54b provides a stepwise detachment of the third embodiment of a skin tag removing device 1" from its adhesive contact with and attachment to the modified holder component 35'. First the adhesive force is initially reduced or even entirely eliminated in the area around the first guide key 46a due to the engagement of first guide key 46a and first shoulder 54a makes the pulling force strongest at this location. Upon further retraction of the applicator head 17' from the hole 38 of the modified holder component 35' the adhesive force in the areas around the first guide key 46a is gradually reduced and a similar "detachment attack" is initiated oppositely, due to the engagement between the second guide key 46b and the second shoulder 54b until the skin tag removing device 1" on the applicator head 17' is completely free of its adhesive contact with the modified holder component 35'. Optionally the opposite "detachment attack" related to the second shoulder 54b is delayed due to being closer to the free tip of the applicator head 17' than the first shoulder 54a.

Thus detachment of the third embodiment of a skin tag removing device 1" from the modified holder component 35' may take place earlier at the first shoulder 54a at the first blind proximal elongate guide groove section 53a of the first second guide groove 49a than at the second shoulder 54b in the second intermediate guide groove section 52b of the second guide groove 49b.

The suitable adhesive for the present invention provides an adhesive force selected to attach the skin tag removing device 1,1',1" firmly with the aperture 9 above the hole 38 of the modified holder component 35' so that the skin tag removing device 1" does not accidentally dislocate when the applicator head 17' passes through the aperture 9 to open the occlusion members 6,7. The adhesive force is however not stronger than the skin tag removing device easily detaches from the modified holder component 35' when the skin tag removing device is retracted as being mounted on the applicator head. A beneficial adhesive is of the kind that has good storage time, does not dry out fast and is easy releasable from a potential protective release liner.

An adhesive configuration of the third embodiment of a skin tag removing device 1" is shown in FIGS. 25, 26 and 27 in form of an adhesive skin tag removing unit 55 including the skin tag removing device 1".

Emphasis is made that an adhesive skin tag removing unit 55 of the present invention may include any of the embodiments of skin tag removing devices 1,1',1" of the present invention and be used with the applicable applicator rod and applicator housing. Shapes, dimensions and thicknesses are only examples and the individual components of an adhesive skin tag removing unit can be given any design that complies with the chosen design of the associated skin tag removing device and does not obstruct and/or complicate the application and use of the skin tag removing device itself in general. Such design confers the beneficial properties to the adhesive skin tag removing unit that it is easy to detach from the modified holder component without the skin tag removing device accidentally gets off the applicator head due to too strong adhesive attachment force between skin tag removing device 1,1',1" and holder component when the skin tag removing device 1,1',1" is to be detached from its adhesive attachment to said holder component.

The adhesive skin tag removing unit 55 used with the skin tag removing device 1,1',1" includes a second release liner 56, a cover 57, and an adhesive layer 58 having adhesive on both sides, e.g. a piece of double-coated tape. In the alternative the skin tag removing device 1,1',1" can be coated with the adhesive where appropriate, such as on at least a part of the skin-contacting side. For the present exemplary embodiment the figure-of-eight-shaped second release liner 56 has a large diameter part 59 to protect a skin adhesive 60 on a skin-contacting surface 61 of the cover 57, and a substantially smaller diameter part 62 comprising a ring-shaped release part 65 around a central release part 66. The ring-shaped release part 65 covers the perimeter 63 of a double-coated adhesive layer 58 and the central release part 66 covers the area bordered by the ring-shaped release part 65.

The adhesive layer 58 has a traverse slot 64 aligned with, or alignable with, and optionally superjacent the aperture 9 of the skin tag removing device 1,1',1". In the present exemplary embodiment the traverse slot 64 is an I-slot, so that the opposite flaps 67a,67b better can open together with the occlusion members 6,7 when the applicator head 17,17' passes through. The area and outline of the double-adhesive layer 58 may expediently be a bit greater than the area and outline of the skin tag removing device 1,1',1" so that the double-adhesive layer 58 provides a smooth protective outer edge 68 beyond the outer perimeter of the base member 2 of the skin tag removing device 1,1',1", and thereby in an easy manner serve to avoid that the skin tag removing device 1,1',1" injures the skin around the skin tag at the site of application of said skin tag removing device 1,1',1", thereby avoiding or at least reducing incidents of a.o. galling, pruritus and redness that could obstruct treatment time.

The ring-shaped release part 65 of the second release liner 56 has a projecting lip or flap 69 to facilitate removal of said second release liner 56.

In the exploded view of FIG. 27 the adhesive layer 58 of the skin tag removing unit 55 has no protective liner at the face opposite the skin tag removing device 1". It is evident that during storage such a protective liner is provided to avoid that the adhesive surface maintains adhesive properties at all times. Such a protective liner can be a separate liner for each skin tag removing unit 55, or several skin tag removing units 55 can share a common protective release sheet 70, as e.g. shown in FIG. 28. In FIG. 28 is shown five skin tag removing units 55 without skin tag removing devices, which can be applied later if desired. Thus FIG. 28 shows the components of an adhesive-protecting release system and a cover of the release system of the skin tag removing unit 55. The large diameter part 59 of the second release liner 56 is not adhered to the protective release sheet 70, so below of the cover 57 is free from adhesive attachment to the protective release sheet 70.

FIG. 29 shows the skin tag removing unit 55 without skin tag removing device 1,1'1" and from its skin-contacting face, thus the face opposite the face exposed to the viewer.

Use of the adhesive skin tag removing unit 55, including how the applicator system is used for application of the skin tag removing device 1,1',1" on a skin tag 42, and how the adhesive skin tag removing unit 55 is utilised for mounting a skin tag removing device 1,1',1" of the present invention in a constrictive, compressing arrangement around the skin tag 42 to be removed, is described with reference to FIGS. 30-40.

Accordingly FIGS. 30-40 show a series of steps for mounting the third embodiment of a skin tag removing device 1" on the applicator head 17', how the third embodiment of a skin tag removing device 1" is ejected to surround the skin tag 42, how attachment of the third embodiment of a skin tag removing device 1" to the skin 43 takes place, and how the third embodiment of a skin tag removing device 1" finally is covered by the cover 57.

FIG. 30 is a perspective view of a fragment of an embodiment of a flexible release structure 71 mounted at a hole of a modified holder component 35'. The flexible release structure 71 of the exemplary embodiment is composed of two opposite release structure parts 72a,72b in form of pleated pieces of release liner, such as silicon-coated paper.

In the perspective fragmentary view of FIG. 31a skin tag removing unit 55 has been taken off the release sheet 70. The skin tag removing unit 55 is then releaseably mounted on the flexible release structure shown in FIG. 30, by means of the adhesive surface of the double-coated adhesive layer 58. As an example the double-coated adhesive layer 58 is shown as being transparent so that the opposite release structure parts 72a,72b can be seen below the I-slot 64. The central release liner part 56 has been removed and a skin tag removing device 1,1',1" can now be mounted, if not being integral with the skin tag removing unit 55 already.

Now, FIGS. 30 and 31 show the preparation steps a)-d) of the method, in which preparation steps a skin tag removing unit 55 is being releaseably mounted on a flexible release structure 71 of two opposite pleated release structure parts 72a,72b on opposites sides of a hole 38, as shown in FIG. 30. In the view of FIG. 31 the ring-shaped release part 65 has been removed from the double-coated adhesive layer 58. The third embodiment of a skin tag removing device 1" on the skin tag removing unit 55 with the cover 57 and double-coated adhesive layer 58 is now ready for its release from the flexible release liner structure 71 for adhesion to the skin 43 around the skin tag 42. To this aspect an applicator of the present invention, as seen in FIGS. 32-38, is very useful.

FIG. 32 shows the applicator head 17' ready to be inserted into the aperture 9 of the third embodiment of a skin tag removing device 1" on the skin tag removing unit 55 for engagement of ridges 32 with occlusion members 6,7, as described for the second embodiment of an applicator rod 17.

As shown in FIG. 33, to begin the engagement step, the tapered tip ends 18a',18b' of the applicator head 17' is positioned above the aperture 9 to be pushed into the hole 38 as seen in FIGS. 34 and 35.

In the situation seen in FIG. 34 the circumferential outlet flange 27 that surrounds the outlet of the second embodiment of a housing 22 is moved in the direction indicated by arrow A towards the modified holder component 35' in contact with the third embodiment of a skin tag removing device 1". The applicator head 17' has penetrated the aperture 9 of the third embodiment of a skin tag removing device 1" on the skin tag removing unit 55 while said skin tag removing unit 55 is adhered to the modified holder component 35' by means of double-coated adhesive layer 58. The flexible release structure 70 is being compacted.

The gap between the flexible release structure parts 72a, 72b of the flexible release structure 71 is aligned and substantially parallel with the aperture 9 between the occlusions members 6,7 of the third embodiment of a skin tag removing device 1" on the skin tag removing unit 55.

When the pressure from the applicator 22,47 continues in the direction A the third embodiment of a skin tag removing device 1" comes slightly along and is moved more or less inside the hole 38 depending on the applied downwards force and the size of the hole in relation to the outline of the skin tag removing device, as seen in FIG. 35. This forcing brings opposite flexible release structure parts 72a,72b to come along slightly down inside the hole 38, which initiate the first detachment of the flexible release structure parts 72a,72b from the double-coated adhesive layer of the skin-contacting face of the third embodiment of a skin tag removing device 1'. Detachment starts at the adhered location that comes deepest inside the hole 38 and may be to same or different degree at the opposite flexible release structure parts 72a,72b. If e.g. one of the flexible release structure parts 72a,72b is smaller than the other the skin tag removing device may be almost completely set free from the smallest flexible release structure part 72a,72b before it is set free from the other one.

The opposite section 58a,58b of adhesive layer 58 around the I-slot stick to the occlusion members 6,7 and are pulled into the hole 38 adhered to said occlusion members. In the figures the adhesive layer is shown as being transparent but this is not mandatory.

In the first release step shown in FIG. 36 the applicator 17',22 is lifted slightly free of the top wall of the modified holder component 35'. The adhesive layer 58, which is attached to the third embodiment of a skin tag removing device 1', is still partly adhered to both the flexible release structure parts 72a,72b, which flexible release structure parts 72a,72b however now expand so that the release of the adhesive layer on the skin-contacting face of the skin tag removing device takes place smoothly, beginning closest to the aperture 9 and ending at the perimeter of the base member 2 until zero contact is achieved and the third embodiment of a skin tag removing device 1" is safely mounted on the applicator head 17', as shown in FIGS. 37 and 38.

When overcoming the adhesive force between the adhesive layer 58 and the flexible release structure 71 upon pulling the applicator 17',22 free of the hole 38 again, the third embodiment of a skin tag removing device 1" can, due to the presence of shoulders 54a,54b of the opposite guide groove 49a,49b, inside which the guide keys 46a,46b of the third embodiment of a skin tag removing device 1" runs, travel a little along the longitudinal applicator axis whereby the third embodiment of a skin tag removing device 1" can become spaced from said outlet flange, e.g. be spaced from said outlet flange a distance corresponding to the distance between the shoulders 54a, 54b.

In FIG. 39a skin tag 42 is arranged in the space 20 between the tapered free tips 18a',18b' of the applicator head 17' below the guideway 23.

In the mounting step of the situation of FIG. 40 the second embodiment of the housing 22 has been displaced along the longitudinal axis of the applicator rod towards the tapered free tips 18a',18b' of the applicator head 17' and the third embodiment of a skin tag removing device 1" is set free so that the occlusion members 6,7 squeeze around the skin tag 42.

FIG. 41 shows the skin tag removing device 1" associated with the skin tag removing unit 55 on a skin tag 42 with the large diameter release liner 59 partly detached from the cover 57.

FIG. 42 shows that the adhesive cover 57 of the skin tag removing unit 55, relieved of the large diameter release liner 59, is being pivoted to cover the occluded skin tag 42 thereby assuming the skin adhering position seen in FIG. 43 where the contour of the skin tag removing device 1" is visualized in dotted line below the adhesive cover 57.

The flexible release structure 71 allows a smooth and gradual detaching of the skin tag removing unit 55 and associated skin tag removing device 1,1',1" from the modified holder component 35', as shown in the subsequent figures. In particular the flexible release structure 71 initiated the detachment at a minor location or even at a small local point or area wherefrom the releasing spreads.

Emphasis is made that the flexible release structure 71 shown in the figures is just an example and that any release structure that can flex to expand away from the modified holder component 35', optionally also be able to move at least a distance inside the hole 38 of the modified holder component 35', is within the scope of the present invention.

The flexible release structure 71 of the exemplary embodiment is composed of two opposite pieces of pleated release liner, such as silicon-coated paper. The opposite pleatings 72a,72b can expand upwards in the direction C away from the modified holder component 35' to same or different extent depending on the force that pulls at them and until this force is released again.

In accordance with the present invention the occluding force on the skin tag sustains due to the tensioning of the pressure members. Therefore the cross section of the pedicle of the skin tag 42 or other transition to the skin narrows and vital blood supply to the skin tag eventually stops completely with the result that the skin tag withers away and separates from the skin surface 43.

What is claimed is:

1. An applicator system (1,1',1";13,28,47;15,22) comprising at least one skin tag removing device (1,1',1") and an applicator (13,28,47;15,22) for application of the at least one skin tag removing device (1,1',1") on a skin tag (42), wherein
   the at least one skin tag removing device (1,1',1") has an aperture (9) delimited by occlusion
   members (6,7;6',7'), and opposite flexible pressure members (3,4;3',4') to apply pressure to the occlusion members (6,7;6',7') towards the aperture (9),
   the applicator (13,28,47;15,22) comprises a housing (15; 22) with a guideway (23) that extends between an inlet (24) and an outlet (25),
   which guideway (23) is provided for receiving at least a part of a reciprocating applicator rod (13;28;47),
   which applicator rod (13;28;47) has a length that is longer than the length of the guideway (23), an applicator end (16) provided with an applicator head (17,17') for engaging the at least one skin tag removing device (1,1',1") when the applicator head (17,17') is moved out of the outlet (25) of the guideway (23) and forced through the aperture (9) of said skin tag removing device (1,1',1"), and an opposite operating end (13) located outside the inlet (24) of the guideway (23), and
   the applicator head (17,17') has a space (20) for accommodating a skin tag,
   wherein the applicator head (17,17') of the applicator end (16) is bifurcated,
   whereby said head (17,17') is divided into two separate opposite branches, parts or legs (19 a, 19 a', 19b, 19b'), and the space (20) is delimited between said at least two separate opposite branches, parts or legs (19 a, 19 a', 19b, 19b') and open in a direction perpendicular to an axis extending through said two separate branches, parts or legs (19 a, 19 a', 19b, 19b').

2. An applicator system (1,1',1";13,28,47;15,22) according to claim 1, wherein the at least one skin tag removing device (1,1',1") comprises a ring-shaped base member (2;2') having a central opening (10), two opposite flexible pressure members (3,4) pivotally attached to the ring-shaped base member (2;2'), each pressure member (3,4) has an associated occlusion member (6,7;6',7') opposite the attachment to the ring-shaped base member (2,2'), the occlusion members (6,7;6',7') are elongated flat rods or webs that are longer than the width or diameter of the central opening (10), the occlusion members (6,7;6'7') protrude towards each other and define in-between them the aperture (9) for inserting the applicator head (17;17').

3. An applicator system (1";47;22) according to claim 1 wherein at least one of the occlusion members (6',7') has a lengthwise reinforcing member (6a',7a'), optionally both opposite occlusion members (6',7') have a lengthwise reinforcing member (6a',7a').

4. An applicator system (1";47;22) according to claim 3, wherein the at least one reinforcing member (6a',7a') is shorter than the occlusion member (6',7').

5. An applicator system (1,1',1";13,28,47;15,22) according to claim 1, wherein the applicator system (1,1',1";13,28, 47;15,22) comprises a skin tag removing unit (55) including an adhesive layer (58) for conferring a skin-adhesive property to the at least one skin tag removing device (1,1',1"), an adhesive cover (57) arranged in a defined position for subsequent coverage of the occluded skin tag, a release liner

(56) on a skin-contacting surface (61) of the adhesive cover (57) or a release liner on one or both surfaces of the adhesive layer (58), and the at least one skin tag removing device (1,1',1") is optionally on the surface of the adhesive layer facing away from the adhesive cover.

6. An applicator system (1,1',1";13,28,47;15,22) according to claim 5, wherein the release liner (56) has a figure-eight-shape, preferably the release liner (56) has a first part (59) that protects a skin adhesive (60) on the skin-contacting surface (61) of the cover (57), said first part (59) has a first diameter that is larger than a diameter of a second part (62), said second part comprises a ring-shaped release part that covers a perimeter (63) of the adhesive layer (58) and a central release part (66) that covers the area bordered by the ring-shaped release part.

7. An applicator system (1,1',1";13,28,47;15,22) according to claim 1, wherein the inlet (24) of the guideway (23) of the housing (15;22) has a first stopper (33;34) for engaging at least one second stopper (30) of the applicator rod (13;28;47) for preventing the applicator rod (13;28;47) from being withdrawn from the guideway (23) when the applicator head (17;17') of the applicator rod (13;28;47) is moved from outside the outlet (25) of the guideway (23) inside said guideway (23).

8. An applicator system (1,1',1";47;15,22) according to claim 1, wherein the applicator head (17') has at least one guide groove (49a,49b) on an exterior face (48a,48b), optionally the applicator head (17') has guide grooves (49a, 49b) on both exterior opposite faces (48a,48b).

9. An applicator system (1";47;22) according to claim 8, wherein the skin tag removing device (1") has at least one guide bead or guide key (46a,46b) that protrudes inside the central opening (10) of the skin tag removing device (1") from the interior diameter of the ring-shaped base member (2), said guide bead or guide key (46a,46b) are configured to engage the at least one guide groove (49a,49b) of the applicator head (17'), optionally the skin tag removing device (1") has at least two opposite guide beads or guide keys.

10. An applicator system (1";47;22) according to claim 8, wherein the at least one guide groove (49a;49b) of the applicator head (17') has a respective key opening (50a;50b) located at a free tip part (18a;18b), wherein the key opening (50a;50b) extends into a respective distal elongate guide groove section (51a;50b), said distal elongate guide groove section (51a;51b) extends into an intermediate guide groove section (52a;50b) that has a width that increases towards a blind proximal elongate guide groove section (53a;53 b), and wherein a shoulder (54a;54b) is located in the at least one_guide groove (49a;49b) of the applicator head (17') at the same or different axial distance from the key opening (50a;50b).

11. An applicator system (1,1',1";13,28,47;15,22) according to claim 1, wherein the housing (15;22) has a circumferential outlet flange (27) surrounding the outlet (25), and optionally a circumferential inlet flange (21) arranged surrounding the inlet (24).

12. An applicator system (1,1',1";13,28,47;15,22) according claim 1, wherein the operating end (14) of the applicator rod (13;28;47) has a finger press button (21), said preferably has an area larger than the area of the inlet (24) of the housing (15;22).

13. An applicator system (1,1',1";13,28,47;15,22) according to claim 1, wherein an exterior surface of at least the applicator head (17;17') of the applicator end (16) has means (32) to temporarily maintain an engaging position of the at least one skin tag removing device (1,1',1") on the applicator head (17;17') of the applicator end (16).

14. An applicator system (1,1',1";13,28,47;15,22) according to claim 1, wherein the applicator system (1,1',1";13,28, 47;15,22) further comprises a holder component (35;35'), said holder component (35;35') has a top wall (37) provided with at least one hole (38) dimensioned to
allow the at least one skin tag removing device (1,1',1") to rest on at least a part of the top wall (37) of the holder component (35;35') along the perimeter of the hole (38) so that the aperture (9) is free to allow the applicator head (17;17') of the applicator end (16) to pass through the aperture (9) of the at least one skin tag removing device (1;1';1") to engage the at least one skin tag removing device (1,1',1") upon displacing the applicator head (17;17') of the applicator rod (13;28;47) out through the outlet (25) of the guideway (23), and
allow the occlusion members (6,7;6',7') to pass below the top wall (37).

15. An applicator system (1,1',1";13,28,47;15,22) according to claim 14, wherein the holder component (35;35') has one or more flexible release structures (71) around the holes (38), and a respective skin tag removing device (1,1',1") or skin tag removing unit (55) is mounted or is mountable to said release structure (71).

16. An applicator system (1,1',1";13,28,47;15,22) according to claim 15, wherein the flexible release structure (71) includes at least two opposite release structure parts (72a, 72b).

17. An applicator system (1,1',1";13,28,47;15,22) according to claim 16, wherein at least one of the opposite release structure parts (72a,72b) is a pleated piece of release liner.

18. A method of operating the applicator system (1,1',1"; 13,28,47;15,22) as defined in claim 1, wherein the method comprises obtaining temporarily engagement between the applicator head (17;17') and the at least one skin tag removing device (1,1',1") by displacing the applicator head (17; 17') of the applicator end (16) of the applicator through the aperture (9) of the at least one skin tag removing device (1,1',1") thereby spreading the occlusion members (6,7;6',7') apart.

19. A method according to claim 18, wherein the method further comprises ejecting the at least one skin tag removing device (1,1',1") by retracting the applicator head (17;17') inside the guideway (23).

20. A method according to claim 18, wherein the method further comprises preparation steps prior to the engagement between the applicator head (17;17') and the at least one skin tag removing device (1,1',1"), wherein
preparation step a) includes: providing the at least one skin tag removing device (1,1',1") as part of or associated with a skin tag removing unit (55), said skin tag removing unit (55) comprises at least an adhesive cover (57) and an adhesive or an adhesive layer (58) for conferring an adhesive property to the at least one skin tag removing device (1,1',1"), and optionally a release liner (56) above one or both of the adhesive of the adhesive cover (57) and the adhesive or adhesive layer (58) adapted for conferring a skin-adhesive property to the at least one skin tag removing device (1,1',1").

21. A method according to claim 18, wherein the method further comprises:
preparation step b) providing a holder component (35,35') with a flexible release liner structure (71) in association with a hole (38) at a top wall (37) of the holder component (35,35'), and preparation step c) adhering the at least one skin tag removing unit (55) to the flexible release liner structure (71).

22. A method according to claim 18, wherein the method further comprises:

preparation step d) removing a release liner (56) on an adhesive or adhesive layer (58) adapted for conferring a skin-adhesive property to the at least one skin tag removing device (1,1',1").

23. A method according to claim 18, wherein the method further comprises a release step after the temporarily engagement between the applicator head (17,17') and the at least one skin tag removing device (1,1',1"), said release step includes moving the applicator with engaged skin tag removing device (1,1',1") upwards from a holder component (35;35') until an adhesive skin-contacting face of the at least one skin tag removing device (1,1',1") is released from its adhesive attachment to a flexible release structure (71).

24. A method according to claim 19, wherein the method further comprises a release step that includes local and/or gradual release of an adhesive skin-contacting face of the at least one skin tag removing device (1,1',1") from its adhesive attachment to a flexible release structure (71) until complete release.

\* \* \* \* \*